(12) United States Patent
Covacci et al.

(10) Patent No.: US 7,141,244 B1
(45) Date of Patent: Nov. 28, 2006

(54) HELICOBACTER PYLORI PROTEINS USEFUL FOR VACCINES AND DIAGNOSTICS

(75) Inventors: Antonello Covacci, Siena (IT); Massimo Bugnoli, Monteriggioni (IT); John Telford, Monteriggioni (IT); Giovanni Macchia, Voorburg (NL); Rino Rappuoli, Sienna (IT)

(73) Assignee: Chiron SRL, Siena (IT)

( * ) Notice: Subject to any disclaimer, the term of this patent is extended or adjusted under 35 U.S.C. 154(b) by 0 days.

(21) Appl. No.: 09/360,685

(22) Filed: Jul. 26, 1999

Related U.S. Application Data

(62) Division of application No. 08/471,491, filed on Jun. 6, 1995, now Pat. No. 6,090,611, which is a division of application No. 08/256,848, filed as application No. PCT/EP93/00472, filed as application No. PCT/EP93/00158 on Jan. 25, 1993, now abandoned.

(30) Foreign Application Priority Data

Mar. 2, 1992 (IT) ............................... FI92A0052

(51) Int. Cl.
*A61K 39/02* (2006.01)
*A61K 39/00* (2006.01)
*A61K 38/00* (2006.01)
*C07K 1/00* (2006.01)
*C07K 2/00* (2006.01)
*C12P 21/04* (2006.01)
*C12N 15/09* (2006.01)

(52) U.S. Cl. ............................... 424/234.1; 424/236.1; 424/190.1; 424/184.1; 424/185.1; 530/350; 530/300; 530/825; 514/2; 435/71.1; 435/69.3

(58) Field of Classification Search ............. 424/130.1, 424/139.1, 150.1, 184.1, 185.1, 234.1, 236.1, 424/190.1; 435/7.1, 69.3, 70.1, 71.2, 252.1, 435/320.1, 71.1, 69.1; 514/44, 2; 530/350, 530/300, 388.4, 825; 536/23.7
See application file for complete search history.

(56) References Cited

U.S. PATENT DOCUMENTS

| | | | |
|---|---|---|---|
| 4,882,271 A | 11/1989 | Evans et al. ................ 435/7 |
| 5,403,924 A | 4/1995 | Cover et al. .............. 536/23.1 |
| 5,541,291 A * | 7/1996 | Keene ...................... 530/350 |
| 5,721,349 A | 2/1998 | Cover et al. .............. 536/22.1 |
| 5,866,375 A * | 2/1999 | Figura et al. ............ 435/71.3 |
| 5,900,372 A * | 5/1999 | Figura et al. ........... 435/252.6 |
| 6,054,132 A * | 4/2000 | Cover et al. ............ 424/184.1 |

FOREIGN PATENT DOCUMENTS

| | | |
|---|---|---|
| EP | 0329570 A2 | 8/1989 |
| EP | 0367644 A1 | 5/1990 |
| WO | WO 87/05943 | 10/1987 |
| WO | WO 89/08843 | 9/1989 |
| WO | WO 90/04030 | 4/1991 |
| WO | WO 91/09049 | 6/1991 |

OTHER PUBLICATIONS

Cover et al. Infection and Immunity, Mar. 1990, vol. 58, No. 3, p. 603-610.*
Peterson et al. Nature 354: 369-373, 1991 (abstract).*
Hirschl et al. Eur. J. Clin. Microbiol. Infect. Dis. 7: 570-575, 1988.*
Petersen et al. Nature 354: 369-373, 1991.*
Hirschl et al. In: *Helicobacter pylori*, gastritis and peptic ulcer. (Ed) Malfertheiner et al. Springer-Verlag, Berlin Heidelberg, 141-146, 1990.*
Harlow et al. In: Antibodies: A Laboratory Manual. Cold Spring Harbor Laboratory, Chapter 5, p. 76, 1988.*
Austin et al., "Structural Comparison of Urease and a GroEl Analog from *Helicobacter pylori*", *J. Bacteriol.*, 1992, 174(22), 7470-7473.
Apel et al., "Antibody Response of Patients Against a 120 kDa Surface Protein of *Campylobacter pylori*", *Aentralblat fur Bakterio. Microb. Und Hygiene*, 1988, 268, 271-276.
Blaser, "Gastric *Campylobacter*-like Organisms, Gastritis, and Peptic Ulcer Disease", *Gastroenterology*, 1987, 93, 371-383.
Blaser, "*Helicobacter pylori*: Its Role in Disease", *Clin. Infect. Dis.*, 1992, 15, 386-391.
Blaser, M., "*H.pylori* associated disease involves host and bacterial factors," *HP World-Wide*, Feb. 1992, 1-8.
Clayton, C.L. et al., "Molecular Cloning Expression of *Campylobacter pylori* Species-Specific Antigens in *Escherichia coli* K-12," *Infection Immunity*, 1989, 57(2), 623-629.
Cover et al., "Purification and Characterization of the Vacuolating Toxin from *Helicobacter pylori*", *J. Biol. Chem.*, 1992, 267(15), 10570-10575.
Cover et al., "Serum Neutralizing Antibody Response to the Vacuolating Cytotoxin of *Helicobacter pylori*", *J. Clin. Invest.*, 1992, 90, 913-918.
Cover et al., "Human serologic response to *Campylobacter pylori* cytotoxin-associated proteins", *Gastroenterology*, 1989, 96 (5/2), A101, abstract.
Crabtree et al., "Expression of 120 kilodalton protein and cytotoxicity in *Helicobacter pylori*", *J. Clin. Pathol.*, 1992, 45, 733-734.
Cussac et al., "Expression of *Helicobacter pylori* Urease Genes in *Escherichia coli* Grown under Nitrogen-Limiting Conditions", *J. Bacteroil.*, 1992, 174(8), 2466-2473.
Dooley et al., "Prevalence of *Helicobacter pylori* Infection and Histologic Gastritis in Asymptomatic Persons", *New Engl. J. Med.*, 1989, 321, 1562-1566.
Drumm et al., "Intrafamilial Clustering of *Helicobacter pylori* Infection", *New Engl. J. Med.*, 1990, 322(6), 359-363.

(Continued)

Primary Examiner—S. Devi
(74) Attorney, Agent, or Firm—Woodcock Washburn LLP

(57) ABSTRACT

This invention provides polypeptides of *Helicobacter pylori* cytotoxin associated immunodominant (CAI) antigen. The invention also provides prophylactic and therapeutic vaccines comprising polypeptides of *Helicobacter pylori* CAI antigen, and methods for their preparation. The invention also provides methods of treatment of *Helicobactor pylori* infection using these vaccines.

55 Claims, 14 Drawing Sheets

OTHER PUBLICATIONS

Dunn et al., "Identification and Purification of a cpn60 Heat Shock Protein Homolog from *Helicobacter pylori*", *Infect. Immun.*, 1992, 60(5), 1946-1951.

Evans et al., "Urease-Associated Heat Shock Protein of *Helicobacter pylori*", *Infect. Immun.*, 1992, 60(5), 2125-2127.

Evans et al., "A Sensitive and Specific Serologic Test for Detection of *Campylobacter pylori* Infection", *Gastroenterology*, 1989, 96, 1004-1008.

Gerstenecker et al., "Serodiagnosis of *Helicobacter pylori* Infections with an Enzyme Immunoassay Using the Chromatographically Purified 120 Kilodalton Protein", *Eur. J. Clin. Microbiol. Infect. Dis.*, 1992, 11(7), 595-601.

Goodwin et al., "Transfer of *Campylobacter pylori* and *Campylobacter mustelae* to *Helicobacter* gen. nov. As *Helicobacter pylori* comb. Nov. And *Helicobacter mustelae* comb. Nov., Respectively," *Int. J. Syst. Bacteriol.*, 1989, 39(4), 397-405.

Graham et al., "Epidemiology of *Helicobacter pylori* in an Asymptomatic Population in the United States", *Gastroenterology*, 1991, 100, 1495-1501.

Graham et al., "Seroepidemiology of *Helicobacter pylori* Infection in India: Comparison of Developing and Developed Countries", *Digestive Diseases and Sciences*, 1991, 36(8), 1084-1088.

Jones et al., "Antibody to the gastric *Campylobacter*-like organism ("*Campylobacter pyloridis*")—Clinical correlations and distribution in the normal population", *Med. Microbiol.*, 1986, 22, 57-62.

Kahn, S. et al., "The major 85-KD surface antigen of the mammalian form of *Trypanosoma cruzi* is encoded by a large heterogeneous family of simultaneously expressed genes," *J. Exp. Med.*, 1990, 172(2), 589-597.

Leunk, "Production of a Cytotoxin by *Helicobacter pylori*", *Rev. Infect. Dis.*, 1991, 13(8), S686-S689.

Leying et al., "Cloning and genetic characterization of a *Helicobacter pylori* flagellin gene", *Mol. Microbiol.*, 1992, 6(19), 2863-2874.

Morris et al., "Seroepidemiology of *Campylobacter pyloridis*", *N.Z. Med. J.*, 1986, 99(809), 657-659.

Orkin, S.H. et al., Report and Recommendations of the Panel to Assess the NIH Investment in Research on Gene Therapy, Dec. 1995, 41 pages.

Parsonnet et al., "*Helicobacter pylori* Infection and the Risk of Gastric Carcinoma", *New Engl. J. Med.*, 1991, 325(16), 1127-1131.

Pei, Z. et al., "Identification Purification and Characterization of Major Antigenic Proteins of Campylobacter-Jejuni," *J. Biol. Chem.*, 1991, 266(25), 16363-16369.

Perez-Perez et al., "Characteristics of *Helicobacter pylori* Variants Selected for Urease Deficiency", *J. Infect. Immun.*, 1992, 60(9), 3658-3663.

Thomas et al., "Isolation of *Helicobacter pylori* from human faeces", *Lancet*, 1992, 340, 1194-1195.

Warren et al., "Unidentified Curved Bacilli on Gastric Epithelium in Active Chronic Gastritis", *Lancet*, 1983, 1273-1275.

Figura, N et al., "Serum antibodies to the vacuolating toxin produced by *Helicobacter pylori*", *Helicobacter pylori, Gastritis and Peptic Ulcer*, Malfertheiner et al. (Eds), Springer Verlag, Berlin, 1990, pp. 169-161.

Gerken, et al., sequence submitted to EST-STS by Utah Center for Human Genome Res. University of Utah, 1993, Accession No. L18544.

Covacci, A. et al., "Molecular characterization of the 128-kDa immunodominant antigen of *Helicobacter pylori* associated with cytotoxicity and duodenal ulcer", *Proc. Natl. Acad. Sci. USA*, 1993, 90(12), 5791-5795.

Tummuru, M.K.R., "Cloning and Expression of a High-Molecular-Mass Mjor Antigen of *Helicobacter pylori*: Evidence of Linkage to Cytotoxin Production", *Infection and Immunity*, 1993, 61(5),1799-1809.

\* cited by examiner

```
   1 AAAAAGAAAG GAAGAAAATG GAAATACAAC AAACACACCG CAAAATCAAT
  51 CGCCCTCTGG TTTCTCTCGC TTTAGTAGGA GCATTAGTCA GCATCACACC
 101 GCAACAAAGT CATGCCGCCT TTTTCACAAC CGTGATCATT CCAGCCATTG
 151 TTGGGGGTAT CGCTACAGGC ACCGCTGTAG GAACGGTCTC AGGGCTTCTT
 201 AGCTGGGGGC TCAAACAAGC CGAAGAAGCC AATAAAACCC CAGATAAACC
 251 CGATAAAGTT TGGCGCATTC AAGCAGGAAA AGGCTTTAAT GAATTCCCTA
 301 ACAAGGAATA CGACTTATAC AGATCCCTTT TATCCAGTAA GATTGATGGA
 351 GGTTGGGATT GGGGGAATGC CGCTAGGCAT TATTGGGTCA AAGGCGGGCA
 401 ACAGAATAAG CTTGAAGTGG ATATGAAAGA CGCTGTAGGG ACTTATACCT
 451 TATCAGGGCT TAGAAACTTT ACTGGTGGGG ATTTAGATGT CAATATGCAA
 501 AAAGCCACTT TACGCTTGGG CCAATTCAAT GGCAATTCTT TTACAAGCTA
 551 TAAGGATAGT GCTGATCGCA CCACGAGAGT GATTTCAACG CTAAAAATAT
 601 CTCAATTGAT AATTTTGCAG AAATCAACAA CTCGTGTGGG TTCTGGAGCC
 651 GGGAGGAAAG CCAGCTCTAC GGTTTTGACT TTGCAAGCTT CAGAAGGGAT
 701 CACTAGCGAT AAAAACGCTG AAATTTCTCT TTATGATGGT GCCACGCTCA
 751 ATTTGGCTTC AAGCAGCGTT AAATTAATGG GTAATGTGTG GATGGGCCGT
 801 TTGCAATACG TGGGAGCGTA TTTGGCCCCT TCATACAGCA CGATAAACAC
 851 TTCAAAAGTA ACAGGGGAAG TGAATTTTAA CCACCTCACT GTTGGCGATA
 901 AAAACGCCGC TCAAGCGGGC ATTATCGCTA ATAAAAAGAC TAATATTGGC
 951 ACACTGGATT TGTGGCAAAG CGCCGGGTTA ACATTATCG CTCCTCCAGA
1001 AGGTGGCTAT AAGGATAAAC CCAATAATAC CCCTTCTCAA AGTGGTGCTA
1051 AAAACGACAA AAATGAAAGC GCTAAAAACG ACAAACAAGA GAGCAGTCAA
1101 AATAATAGTA ACACTCAGGT CATTAACCCA CCCAATAGTG CGCAAAAAAC
1151 AGAAGTTCAA CCCACGCAAG TCATTGATGG GCCTTTTGCG GGCGGCAAAG
1201 ACACGGTTGT CAATATCAAC CGCATCAACA CTAACGCTGA TGGCACGATT
1251 AGAGTGGGAG GGTTTAAAGC TTCTCTTACC ACCAATGCGG CTCATTTGCA
1301 TATCGGCAAA GGCGGTGTCA ATCTGTCCAA TCAAGCGAGC GGGCGCTCTC
```

FIG. 1A

```
1351 TTATAGTGGA AAATCTAACT GGGAATATCA CCGTTGATGG GCCTTTAAGA
1401 GTGAATAATC AAGTGGGTGG CTATGCTTTG GCAGGATCAA GCGCGAATTT
1451 TGAGTTTAAG GCTGGTACGG ATACCAAAAA CGGCACAGCC ACTTTTAATA
1501 ACGATATTAG TCTGGGAAGA TTTGTGAATT TAAAGGTGGA TGCTCATACA
1551 GCTAATTTTA AAGGTATTGA TACGGGTAAT GGTGGTTTCA ACACCTTAGA
1601 TTTTAGTGGC GTTACAGACA AAGTCAATAT CAACAAGCTC ATTACGGCTT
1651 CCACTAATGT GGCCGTTAAA AACTTCAACA TTAATGAATT GATTGTTAAA
1701 ACCAATGGGA TAAGTGTGGG GGAATATACT CATTTTAGCG AAGATATAGG
1751 CAGTCAATCG CGCATCAATA CCGTGCGTTT GGAAACTGGC ACTAGGTCAC
1801 TTTTCTCTGG GGGTGTTAAA TTTAAAGGTG GCGAAAAATT GGTTATAGAT
1851 GAGTTTTACT ATAGCCCTTG GAATTATTTT GACGCTAGAA ATATTAAAAA
1901 TGTTGAAATC ACCAATAAAC TTGCTTTTGG ACCTCAAGGA AGTCCTTGGG
1951 GCACATCAAA ACTTATGTTC AATAATCTAA CCCTAGGTCA AAATGCGGTC
2001 ATGGATTATA GCCAATTTTT AAATTTAACC ATTCAAGGGG ATTTCATCAA
2051 CAATCAAGGC ACTATCAACT ATCTGGTCCG AGGTGGGAAA GTGGCAACCT
2101 TAAGCGTAGG CAATGCAGCA GCTATGATGT TAATAATGA TATAGACAGC
2151 GCGACCGGAT TTTACAAACC GCTCATCAAG ATTAACAGCG CTCAAGATCT
2201 CATTAAAAAT ACAGAACATG TTTTATTGAA AGCGAAAATC ATTGGTTATG
2251 GTAATGTTTC TACAGGTACC AATGGCATTA GTAATGTTAA TCTAGAAGAG
2301 CAATTCAAAG AGCGCCTAGC CCTTTATAAC AACAATAACC GCATGGATAC
2351 TTGTGTGGTG CGAAATACTG ATGACATTAA AGCATGCGGT ATGGCTATCG
2401 GCGATCAAAG CATGGTGAAC AACCCTGACA ATTACAAGTA TCTTATCGGT
2451 AAGGCATGGA AAAATATAGG GATCAGCAAA ACAGCTAATG CTCTAAAAT
2501 TTCGGTGTAT TATTTAGGCA ATTCTACGCC TACTGAGAAT GGTGGCAATA
2551 CCACAAATTT ACCCACAAAC ACCACTAGCA ATGCACGTTC TGCCAACAAC
2601 GCCCTTGCAC AAAACGCTCC TTTCGCTCAA CCTAGTGCTA CTCCTAATTT
2651 AGTCGCTATC AATCAGCATG ATTTTGGCAC TATTGAAAGC GTGTTTGAAT
```

FIG. 1B

2701 TGGCTAACCG CTCTAAAGAT ATTGACACGC TTTATGCTAA CTCAGGCGCT
2751 CAAGGCAGGG ATCTCTTACA AACCTTATTG ATTGATAGCC ATGATGCGGG
2801 TTATGCCAGA AAAATGATTG ATGCTACAAG CGCTAATGAA ATCACCAAGC
2851 AATTGAATAC GGCCACTACC ACTTTAAACA ACATAGCCAG TTTAGAGCAT
2901 AAAACCAGCG GCTTACAAAC TTTGAGCTTG AGTAATGCGA TGATTTTAAA
2951 TTCTCGTTTA GTCAATCTCT CCAGGAGACA CACCAACCAT ATTGACTCGT
3001 TCGCCAAACG CTTACAAGCT TTAAAAGACC AAAAATTCGC TTCTTTAGAA
3051 AGCGCGGCAG AAGTGTTGTA TCAATTTGCC CCTAAATATG AAAAACCTAC
3101 CAATGTTTGG GCTAACGCTA TTGGGGGAAC GAGCTTGAAT AATGGCTCTA
3151 ACGCTTCATT GTATGGCACA AGCGCGGGCG TAGACGCTTA CCTTAACGGG
3201 CAAGTGGAAG CCATTGTGGG CGGTTTTGGA AGCTATGGTT ATAGCTCTTT
3251 TAATAATCGT GCGAACTCCC TTAACTCTGG GGCCAATAAC ACTAATTTTG
3301 GCGTGTATAG CCGTATTTTA ACCAACCAGC ATGAATTTGA CTTTGAAGCT
3351 CAAGGGGCAC TAGGGAGCGA TCAATCAAGC TTGAATTTCA AAAGCGCTCT
3401 ATTACAAGAT TTGAATCAAA GCTATCATTA CTTAGCCTAT AGCGCTGCAA
3451 CAAGAGCGAG CTATGGTTAT GACTTCGCGT TTTTTAGGAA CGCTTTAGTG
3501 TTAAAACCAA GCGTGGGTGT GAGCTATAAC CATTTAGGTT CAACCAACTT
3551 TAAAAGCAAC AGCACCAATC AAGTGGCTTT GAAAAATGGC TCTAGCAGTC
3601 AGCATTTATT CAACGCTAGC GCTAATGTGG AAGCGCGCTA TTATTATGGG
3651 GACACTTCAT ACTTCTACAT GAATGCTGGA GTTTTACAAG AGTTCGCTCA
3701 TGTTGGCTCT AATAACGCCG CGTCTTTAAA CACCTTTAAA GTGAATGCCG
3751 CTCGCAACCC TTTAAATACC CATGCCAGAG TGATGATGGG TGGGGAATTA
3801 AAATTAGCTA AGAAGTGTT TTTGAATTTG GGCGTTGTTT ATTTGCACAA
3851 TTTGATTTCC AATATAGGCC ATTTCGCTTC CAATTTAGGA ATGAGGTATA
3901 GTTTCTAAAT ACCGCTCTTA AACCCATGCT CAAAGCATGG GTTTGAAATC
3951 TTACAAAACA

FIG. 1C

```
   1 MEIQQTHRKI NRPLVSLALV GALVSITPQQ SHAAFFTTVI IPAIVGGIAT
  51 GTAVGTVSGL LSWGLKQAEE ANKTPDKPDK VWRIQAGKGF NEFPNKEYDL
 101 YRSLLSSKID GGWDWGNAAR HYWVKGGQQN KLEVDMKDAV GTYTLSGLRN
 151 FTGGDLDVNM QKATLRLGQF NGNSFTSYKD SADRTTRVIS TLKISQLIIL
 201 QKSTTRVGSG AGRKASSTVL TLQASEGITS DKNAEISLYD GATLNLASSS
 251 VKLMGNVWMG RLQYVGAYLA PSYSTINTSK VTGEVNFNHL TVGDKNAAQA
 301 GIIANKKTNI GTLDLWQSAG LNIIAPPEGG YKDKPNNTPS QSGAKNDKNE
 351 SAKNDKQESS QNNSNTQVIN PPNSAQKTEV QPTQVIDGPF AGGKDTVVNI
 401 NRINTNADGT IRVGGFKASL TTNAAHLHIG KGGVNLSNQA SGRSLIVENL
 451 TGNITVDGPL RVNNQVGGYA LAGSSANFEF KAGTDTKNGT ATFNNDISLG
 501 RFVNLKVDAH TANFKGIDTG NGGFNTLDFS GVTDKVNINK LITASTNVAV
 551 KNFNINELIV KTNGISVGEY THFSEDIGSQ SRINTVRLET GTRSLFSGGV
 601 KFKGGEKLVI DEFYYSPWNY FDARNIKNVE ITNKLAFGPQ GSPWGTSKLM
 651 FNNLTLGQNA VMDYSQFLNL TIQGDFINNQ GTINYLVRGG KVATLSVGNA
 701 AAMMFNNDID SATGFYKPLI KINSAQDLIK NTEHVLLKAK IIGYGNVSTG
 751 TNGISNVNLE EQFKERLALY NNNNRMDTCV VRNTDDIKAC GMAIGDQSMV
 801 NNPDNYKYLI GKAWKNIGIS KTANGSKISV YYLGNSTPTE NGGNTTNLPT
 851 NTTSNARSAN NALAQNAPFA QPSATPNLVA INQHDFGTIE SVFELANRSK
 901 DIDTLYANSG AQGRDLLQTL LIDSHDAGYA RKMIDATSAN EITKQLNTAT
 951 TTLNNIASLE HKTSGLQTLS LSNAMILNSR LVNLSRRHTN HIDSFAKRLQ
1001 ALKDQKFASL ESAAEVLYQF APKYEKPTNV WANAIGGTSL NNGSNASLYG
1051 TSAGVDAYLN GQVEAIVGGF GSYGYSSFNN RANSLNSGAN NTNFGVYSRI
1101 LTNQHEFDFE AQGALGSDQS SLNFKSALLQ DLNQSYHYLA YSAATRASYG
1151 YDFAFFRNAL VLKPSVGVSY NHLGSTNFKS NSTNQVALKN GSSSQHLFNA
1201 SANVEARYYY GDTSYFYMNA GVLQEFAHVG SNNAASLNTF KVNAARNPLN
1251 THARVMMGGE LKLAKEVFLN LGVVYLHNLI SNIGHFASNL GMRYSF
```

FIG. 2

```
CTCCATTTTAAGCAACTCCATAGACCACTAAAGAAACTTTTTTTGAGGCTATCTTTGAAA
GCTTAATTATACATGCTATAGTAAGCATGACACACAAACCAAACTATTTTTAGAACGCTT
TCAAAAAGATTCATTTCTTATTTCTTGTTCTTATTAAAGTTCTTTCATTTTAGCAAATTT
CTTTTTTCAATATTAATAATGATTAATGAAAAAAAAAAAAAATGCTTGATATTGTTGTAT
TTGACACTAACAAGATACCGATAGGTATGAAACTAGGTATAGTAAGGAGAAACAATGACT
                                                          M  T
         AATAATCTTCAAGTAGCTTTTCTTAAAGTTGATAACGCTGTCGCTTCATACGATCCTGAT
      23 N  N  L  Q  V  A  F  L  K  V  D  N  A  V  A  S  Y  D  P  D
         CAATTAAGGGAAGAATACTCCAATAAAGCGATCAAAAATCCTACCAAAAAGAATCAGTAT
      63 Q  L  R  E  E  Y  S  N  K  A  I  K  N  P  T  K  K  N  Q  Y
         GAATCTTCCACAAAGAGCTTTCAGAAATTTGGGGATCAGCGTTACCGAATTTTCACAAGT
     103 E  S  S  T  K  S  F  Q  K  F  G  D  Q  R  Y  R  I  F  T  S
         GAAAATATCATACAACCCCCTATCCTTGATGATAAAGAGAAAGCGGAGTTTTTGAAATCT
     143 E  N  I  I  Q  P  P  I  L  D  D  K  E  K  A  E  F  L  K  S
         ATGGGCGTGTTTGATGAGTCCTTGAAAGAAAGGCAAGAAGCAGAAAAAAATGGAGAGCCT
     183 M  G  V  F  D  E  S  L  K  E  R  Q  E  A  E  K  N  G  E  P
         GATGTCAAAGAAGCAATCAATCAAGAACCAGTTCCCCATGTCCAACCAGATATAGCCACT
     223 D  V  K  E  A  I  N  Q  E  P  V  P  H  V  Q  P  D  I  A  T
         AATTTTTCTAAATTCACTCTTGGCGATATGGAAATGTTAGATGTTGAGGGAGTCGCTGAC
     263 N  F  S  K  F  T  L  G  D  M  E  M  L  D  V  E  G  V  A  D
         TTAATGGGGAGTCATAATGGCATAGAACCTGAAAAAGTTTCATTGTTGTATGGGGGCAAT
     303 L  M  G  S  H  N  G  I  E  P  E  K  V  S  L  L  Y  G  G  N
         AACAATGTGGCTACAATAATTAATGTGCATATGAAAAACGGCAGTGGCTTAGTCATAGCA
     343 N  N  V  A  T  I  I  N  V  H  M  K  N  G  S  G  L  V  I  A
         GGCTCACAACGAGCATTAAGTCAAGAAGAGATCCAAAACAAAATAGATTTCATGGAATTT
     383 G  S  Q  R  A  L  S  Q  E  E  I  Q  N  K  I  D  F  M  E  F
         ACTGAGATTAAAGATTTCCAAAAAGACTCTAAGGCTTATTTAGACGCCCTAGGGAATGAT
     423 T  E  I  K  D  F  Q  K  D  S  K  A  Y  L  D  A  L  G  N  D
         AATGGGGATTTGAGCTACACTCTCAAAGATTATGGGAAAAAAGCAGATAAAGCTTTAGAT
     463 N  G  D  L  S  Y  T  L  K  D  Y  G  K  K  A  D  K  A  L  D
         TATTCTAATTTCAAATACACCAACGCCTCCAAGAATCCCAATAAGGGTGTAGGCGTTACG
```

FIG. 4A

```
ATCTGTCCTATTGATTTGTTTTCCATTTTGTTTCCCATGTGGATCTTGTGGATCACAAAC    120
CATGTGCTCACCTTGACTAACCATTTCTCCAACCATACTTTAGCGTTGCATTTGATTTCT    240
TTGTTAATTGTGGGTAAAAATGTGAATCGTCCTAGCCTTTAGACGCCTGCAACGATCGGG    360
AATGAGAATGTTCAAAGACATGAATTGACTACTCAAGCGTGTAGCGATTTTTAGCAGTCT    480
AACGAAACCATTGACCAACAACCACAAACCGAAGCGGCTTTTAACCCGCAGCAATTTATC    600
 N  E  T  I  D  Q  Q  P  Q  T  E  A  A  F  N  P  Q  Q  F  I
CAAAAACCAATCGTTGATAAGAACGATAGGGATAACAGGCAAGCTTTTGAAGGAATCTCG    720
 Q  K  P  I  V  D  K  N  D  R  D  N  R  Q  A  F  E  G  I  S
TTTTCAGACTTTATCAATAAGAGCAATGATTTAATCAACAAAGACAATCTCATTGATGTA    840
 F  S  D  F  I  N  K  S  N  D  L  I  N  K  D  N  L  I  D  V
TGGGTGTCCCATCAAAACGATCCGTCTAAAATCAACACCCGATCGATCCGAAATTTTATG    960
 W  V  S  H  Q  N  D  P  S  K  I  N  T  R  S  I  R  N  F  M
GCCAAACAATCTTTTGCAGGAATCATTATAGGGAATCAAATCCGAACGGATCAAAAGTTC    1080
 A  K  Q  S  F  A  G  I  I  I  G  N  Q  I  R  T  D  Q  K  F
ACTGGTGGGGATTGGTTGGATATTTTTCTCTCATTTATATTTGACAAAAAACAATCTTCT    1200
 T  G  G  D  W  L  D  I  F  L  S  F  I  F  D  K  K  Q  S  S
ACCACCACCGACATACAAGGCTTACCGCCTGAAGCTAGAGATTTACTTGATGAAAGGGGT    1320
 T  T  T  D  I  Q  G  L  P  P  E  A  R  D  L  L  D  E  R  G
ATTGATCCCAATTACAAGTTCAATCAATTATTGATTCACAATAACGCTCTGTCTTCTGTG    1440
 I  D  P  N  Y  K  F  N  Q  L  L  I  H  N  N  A  L  S  S  V
GGTGGTCCTGGAGCTAGGCATGATTGGAACGCCACCGTTGGTTATAAAGACCAACAAGGC    1560
 G  G  P  G  A  R  H  D  W  N  A  T  V  G  Y  K  D  Q  Q  G
GGTGGTGAGAAAGGGATTAACAACCCTAGTTTTTATCTCTACAAAGAAGACCAACTCACA    1680
 G  G  E  K  G  I  N  N  P  S  F  Y  L  Y  K  E  D  Q  L  T
CTTGCACAAAATAATGCTAAATTAGACAACTTGAGCGAGAAAGAGAAGGAAAAATTCCGA    1800
 L  A  Q  N  N  A  K  L  D  N  L  S  E  K  E  K  E  K  F  R
CGTATTGCTTTTGTTTCTAAAAAAGACACAAAACATTCAGCTTTAATTACTGAGTTTGGT    1920
 R  I  A  F  V  S  K  K  D  T  K  H  S  A  L  I  T  E  F  G
AGGGAGAAAAATGTTACTCTTCAAGGTAGCCTAAAACATGATGGCGTGATGTTTGTTGAT    2040
 R  E  K  N  V  T  L  Q  G  S  L  K  H  D  G  V  M  F  V  D
AATGGCGTTTCCCATTTAGAAGTAGGCTTTAACAAGGTAGCTATCTTTAATTTGCCTGAT    2160
```

FIG. 4B

```
503 Y  S  N  F  K  Y  T  N  A  S  K  N  P  N  K  G  V  G  V  T
    TTAAATAATCTCGCTATCACTAGTTTCGTAAGGCGGAATTTAGAGGATAAACTAACCACT
543 L  N  N  L  A  I  T  S  F  V  R  R  N  L  C  D  K  L  T  T
    GAATTGGTTGGAAAAACTTTAAACTTCAATAAAGCTGTAGCTGACGCTAAAAACACAGGC
583 E  L  V  G  K  T  L  N  F  N  K  A  V  A  D  A  K  N  T  G
    CATTTAGAGAAAGAAGTAGAGAAAAAATTGGAGAGCAAAAGCGGCAACAAAAATAAAATG
623 H  L  E  K  E  V  E  K  K  L  E  S  K  S  G  N  K  N  K  M
    GCTAATAGAGACGCAAGAGCAATCGCTTACGCTCAGAATCTTAAAGGCATCAAAAGGGAA
663 A  N  R  D  A  R  A  I  A  Y  A  Q  N  L  K  G  I  K  R  E
    GAATTCAAAAATGGCAAAAATAAGGATTTCAGCAAGGCAGAAGAAACACTAAAAGCCCTT
703 E  F  K  N  G  K  N  K  D  F  S  K  A  E  E  T  L  K  A  L
    AATGCAGCTTTGAATGAATTCAAAAATGGCAAAAATAAGGATTTCAGCAAGGTAACGCAA
743 N  A  A  L  N  E  F  K  N  G  K  N  K  D  F  S  K  V  T  Q
    AAAGTTGATAATCTCAATCAAGCGGTATCAGTGGCTAAAGCAACGGGTGATTTCAGTAGG
783 K  V  D  N  L  N  Q  A  V  S  V  A  K  A  T  G  D  F  S  R
    CAAAAAAATGAAAGTCTCAATGCTAGAAAAAAATCTGAAATATATCAATCCGTTAAGAAT
823 Q  K  N  E  S  L  N  A  R  K  K  S  E  I  Y  Q  S  V  K  N
    AAAAACTTTTCGGACATCAAGAAAGAGTTGAATGCAAAACTTGGAAATTTCAATAACAAT
863 K  N  F  S  D  I  K  K  E  L  N  A  K  L  G  N  F  N  N  N
    CAAGCAGCTAGCCTTGAAGAACCCATTTACGCTCAAGTTGCTAAAAAGGTAAATGCAAAA
903 Q  A  A  S  L  E  E  P  I  Y  A  Q  V  A  K  K  V  N  A  K
    CCTTTGAAAAGGCATGATAAAGTTGATGATCTCAGTAAGGTAGGGCTTTCAAGGAATCAA
943 P  L  K  R  H  D  K  V  D  D  L  S  K  V  G  L  S  R  N  Q
    TTTGGCAATCTAGAGCAAACGATAGACAAGCTCAAAGATTCTACAAAACACAATCCCATG
983 F  G  N  L  E  Q  T  I  D  K  L  K  D  S  T  K  H  N  P  M
    TACGCTACTAACAGCCACATACGCATTAATAGCAATATCAAAAATGGAGCAATCAATGAA
```

FIG. 4C

```
       N  G  V  S  H  L  E  V  G  F  N  K  V  A  I  F  N  L  P  D
AAAGGATTGTCCCCACAAGAAGCTAATAAGCTTATCAAAGATTTTTTGAGCAGCAACAAA   2280
    K  G  L  S  P  Q  E  A  N  K  L  I  K  D  F  L  S  S  N  K
AATTATGATGAAGTGAAAAAAGCTCAGAAAGATCTTGAAAAATCTCTAAGGAAACGAGAG   2400
    N  Y  D  E  V  K  K  A  Q  K  D  L  E  K  S  L  R  K  R  E
GAAGCAAAAGCTCAAGCTAACAGCCAAAAAGATGAGATTTTTGCGTTGATCAATAAAGAG   2520
    E  A  K  A  Q  A  N  S  Q  K  D  E  I  F  A  L  I  N  K  E
TTGTCTGATAAACTTGAAAATGTCAACAAGAATTTGAAAGACTTTGATAAATCTTTTGAT   2640
    L  S  D  K  L  E  N  V  N  K  N  L  K  D  F  D  K  S  F  D
AAAGGTTCGGTGAAAGATTTAGGTATCAATCCAGAATGGATTTCAAAAGTTGAAAACCTT   2760
    K  G  S  V  K  D  L  G  I  N  P  E  W  I  S  K  V  E  N  L
GCAAAAAGCGACCTTGAAAATTCCGTTAAAGATGTGATCATCAATCAAAAGGTAACGGAT   2880
    A  K  S  D  L  E  N  S  V  K  D  V  I  I  N  Q  K  V  T  D
GTAGAGCAAGCGTTAGCCGATCTCAAAAATTTCTCAAAGGAGCAATTGGCCCAACAAGCT   3000
    V  E  Q  A  L  A  D  L  K  N  F  S  K  E  Q  L  A  Q  Q  A
GGTGTGAATGGAACCCTAGTCGGTAATGGGTTATCTCAAGCAGAAGCCACAACTCTTTCT   3120
    G  V  N  G  T  L  V  G  N  G  L  S  Q  A  E  A  T  T  L  S
AACAATAATGGACTCAAAAACGAACCCATTTATGCTAAAGTTAATAAAAAGAAAGCAGGG   3240
    N  N  N  G  L  K  N  E  P  I  Y  A  K  V  N  K  K  K  A  G
ATTGACCGACTCAATCAAATAGCAAGTGGTTTGGGTGTTGTAGGGCAAGCAGCGGGCTTC   3360
    I  D  R  L  N  Q  I  A  S  G  L  G  V  V  G  Q  A  A  G  F
GAATTGGCTCAGAAAATTGACAATCTCAATCAAGCGGTATCAGAAGCTAAAGCAGGTTTT   3480
    E  L  A  Q  K  I  D  N  L  N  Q  A  V  S  E  A  K  A  G  F
AATCTATGGGTTGAAAGTGCAAAAAAAGTACCTGCTAGTTTGTCAGCGAAACTAGACAAT   3600
    N  L  W  V  E  S  A  K  K  V  P  A  S  L  S  A  K  L  D  N
AAAGCGACCGGCATGCTAACGCAAAAAAACCCTGAGTGGCTCAAGCTCGTGAATGATAAG   3720
```

FIG. 4D

```
1023 Y  A  T  N  S  H  I  R  I  N  S  N  I  K  N  G  A  I  N
     ATAGTTGCGCATAATGTAGGAAGCGTTCCTTTGTCAGAGTATGATAAAATTGGCTTC
1063 I  V  A  H  N  V  G  S  V  P  L  S  E  Y  D  K  I  G  F
     GTAAAAGACACTAATTCTGGCTTTACGCAATTTTTAACCAATGCATTTTCTACAGCA
1103 V  K  D  T  N  S  G  F  T  Q  F  L  T  N  A  F  S  T  A
     GGTTTCCAAAAATCTTAAAGGATTAAGGAATACCAAAAACGCAAAAACCACCCCTTG
1143 G  F  Q  K  S
     TGAATGCTACCAATTCATGGTATCATATCCCCATACATTCGTATCTAGCGTAGGAAG
     AACTCTGTAAAATCCCTATTATAGGGACACAGAGTGAGAACCAAACTCTCCCTACGG
     GACAGACACTAACGAAAGGCTTTGTTCTTTAAAGTCTGCATGGATATTTCCTACCCC
     CGAAAATTAATTAAGGGTTATAAAGAGAGCATAAACTAGAAAAAACAAGTAGCTATA
     GAAAAATCAGAAAAACCATAGGAATTATCACACCTTATAATGCCCAAAAAAGACGCT
     ATGCCTTTCAAGGTGAAGAGGCAGATATTATTATTTATTCCACCGTGAAAACTTGTG
     ATCTCATTTTTGTGGGTAAAAAGTCTTTCTTTGAGAATTTATGAAGCGATGAGAAGA
     CATTCTTCGCTTCAAAACGCTTTCATAAATCTCTCTAAAGCGCTTTATAATCAACAC
     TTATTAGCGTTACAATTTGAGCCATTCTTTAGCTTGTTTTTCTAGCCAGATCACATC
     CTGCAAATATCCTACAATAGCATCGCCCGAATGGATGAGTAGGGGGGGTGTTGAAAG
     TAAAATAATCACTTCGGGAAAATCTTTAAGGGAGTGAAATAATAACGCATGCAAGTT
     TGCGAAACATTCAAATAGCCTTGTTGTTTCAGGGCATTGTCATAAGCGTTGGATTGG
     GCTAAAATGCTTGGCTCAATCACGCCCACAATAGGGATTTTGGAATGCTTTTGCATC
     TTGAAAAAATCCAAAGCCTCTAAGCCAAATTGCTTGATCGTAGTGGGGTCTTTAGTG
     AGGCTTTTTAAAACGCTAAACCCTCCCACACCGCTATCAAAAACGCCTATTTTCATG
     TCTTCATTGTCCTTAGTTTGTTGCATTTTAGAATAGACAAAGCTT 5925
```

FIG. 4E

```
          E  K  A  T  G  M  L  T  Q  K  N  P  E  W  L  K  L  V  N  D  K
AACCAGAAGAATATGAAAGATTATTCTGATTCGTTCAAGTTTTCCACCAAGTTGAACAATGCT    3840
 N  Q  K  N  M  K  D  Y  S  D  S  F  K  F  S  T  K  L  N  N  A
TCTTATTACTGCTTGGCGAGAGAAAATGCGGAGCATGGAATCAAGAACGTTAATACAAAAGGT    3960
  S  Y  Y  C  L  A  R  E  N  A  E  H  G  I  K  N  V  N  T  K  G
CTAAAAGCGAGGGGTTTTTTAATACTCCTTAGCAGAAATCCCAATCGTCTTTAGTATTTGGGA    4080

TGTGCAAAGTTACGCCTTTGGAGATATGATGTGTGAGACCTGTAGGGAATGCGTTGGAGCTCA    4200
GCAACATCAGCCTAGGAAGCCCAATCGTCTTTAGCGGTTGGGCACTTCACCTTAAAATATCCC    4320
AAAAAGACTTAACCCTTTGCTTAAAATTAAGTTTGATTGTGCTAGTGGGTTCGTGCTATAGTG    4440
ACAAAGATCAAGTTCAAAAAATCATAGAGCTTTTAGAGCAAATTGATCGCGCTCTTAACCAAA    4560
TGCGATCAGAAGTGGAAAAATACGGCTTCAAGAATTTTGATGAGCTCAAAATAGACACTGTGG    4680
GTAATCTTTCTTTCTTGCTAGATTCTAAACGCTTGAATGTGGCTATTTCTAGGGCAAAAGAAA    4800
ATATCTTTAGCGCTATTTTGCAAGTCTGTAGATAGGTAATCTTTTCCAAAGATAATCATTAGA    4920
AATACCCTTATAGTGTGAGCTATAGCCCCTTTTTGGGAATTGAGTTATTTTGACTTTAAATTT    5040
GCCGCTCGCATGAAATTCCACTTTAGGGAATGCGTGTGCATTTTTTTTAAGGGCGTATTTTTG    5160
GGCAAAATGCTCCATAAAATAGCCCTCAATTTTTTGAGCGATTAAGGGAAAATGCGTGCAACC    5280
TCTAACAATTCGCCCTCTAAAATACTTTCTTCAATCAAAGGCACAAAAAGAGAAGTGGCTAAA    5400
ATCGTCGCTTTTGTCCCTAGCACTAAAATAGGGGCGTTTTTATCTTTTACTTGTCGCTTGATC    5520
TCTTCTAAAGCTAGAGCGCTCGCTGTGTTGCATGCCACAATCAATAATTCAATCTGGTGCGGT    5640
CCATAAGGCAGTCTAGCCGTATCGCCATAATAGATGATTTCATCAAATAATTGCGCTTTTAAA    5760
ACACTTTTTTAATTTAATGGGATTAATTAGGGATTTTATTTTTCATTCATTAAGTTTAAAAAT    5880
```

FIG. 4F

```
                10                        30                        50
AAGCTTGCTGTCATGATCACAAAAAACACTAAAAAACATTATTATTAAGGATACAAAATG
                                                            M
                70                        90                       110
GCAAAAGAAATCAAATTTTCAGATAGTGCGAGAAACCTTTTATTTGAAGGCGTGAGGCAA
 A  K  E  I  K  F  S  D  S  A  R  N  L  L  F  E  G  V  R  Q
               130                       150                       170
CTCCATGACGCTGTCAAAGTAACCATGGGGCCAAGAGGCAGGAATGTATTGATCCAAAAA
 L  H  D  A  V  K  V  T  M  G  P  R  G  R  N  V  L  I  Q  K
               190                       210                       230
AGCTATGGCGCTCCAAGCATCACCAAAGACGGCGTGAGCGTGGCTAAAGAGATTGAATTA
 S  Y  G  A  P  S  I  T  K  D  G  V  S  V  A  K  E  I  E  L
               250                       270                       290
AGTTGCCCAGTAGCTAACATGGGCGCTCAACTCGTTAAAGAAGTAGCGAGCAAAACCGCT
 S  C  P  V  A  N  M  G  A  Q  L  V  K  E  V  A  S  K  T  A
               310                       330                       350
GATGCTGCCGGCGATGGCACGACCACAGCGACCGTGCTAGCTTATAGCATTTTTAAAGAA
 D  A  A  G  D  G  T  T  T  A  T  V  L  A  Y  S  I  F  K  E
               370                       390                       410
GGTTTGAGGAATATCACGGCTGGGGCTAACCCTATTGAAGTGAAACGAGGCATGGATAAA
 G  L  R  N  I  T  A  G  A  N  P  I  E  V  K  R  G  M  D  K
               430                       450                       470
GCTGCTGAAGCGATCATTAATGAGCTTAAAAAAGCGAGCAAAAAAGTAGGCGGTAAAGAA
 A  A  E  A  I  I  N  E  L  K  K  A  S  K  K  V  G  G  K  E
               490                       510                       530
GAAATCACCCAAGTGGCGACCATTTCTGCAAACTCCGATCACAATATCGGGAAACTCATC
 E  I  T  Q  V  A  T  I  S  A  N  S  D  H  N  I  G  K  L  I
               550                       570                       590
GCTGACGCTATGGAAAAAGTGGGTAAAGACGGCGTGATCACCGTTGAGGAAGCTAAGGGC
 A  D  A  M  E  K  V  G  K  D  G  V  I  T  V  E  E  A  K  G
               610                       630                       650
ATTGAAGATGAATTGGATGTCGTAGAAGGCATGCAATTTGATAGAGGCTACCTCTCCCCT
 I  E  D  E  L  D  V  V  E  G  M  Q  F  D  R  G  Y  L  S  P
```

FIG. 5A

```
                670                690                  710
TATTTTGTAACGAACGCTGAGAAAATGACCGCTCAATTGGATAATGCTTACATCCTTTTA
 Y  F  V  T  N  A  E  K  M  T  A  Q  L  D  N  A  Y  I  L  L
                730                750                770
ACGGATAAAAAAATCTCTAGCATGAAAGACATTCTCCCGCTACTAGAAAAAACCATGAAA
 T  D  K  K  I  S  S  M  K  D  I  L  P  L  L  E  K  T  M  K 790                810              HindIII
GAGGGCAAACCGCTTTTAATCATCGCTGAAGACATTGAGGGCGAAGCTTTAACGACTCTA
 E  G  K  P  L  L  I  I  A  E  D  I  E  G  E  A  L  T  T  L
                850                870                890
GTGGTGAATAAATTAAGAGGCGTGTTGAATATCGCAGCGGTTAAAGCTCCAGGCTTTGGG
 V  V  N  K  L  R  G  V  L  N  I  A  A  V  K  A  P  G  F  G
                910                930                950
GACAGAAGAAAAGAAATGCTCAAAGACATCGCTATTTTAACCGGCGGTCAAGTCATTAGC
 D  R  R  K  E  M  L  K  D  I  A  I  L  T  G  G  Q  V  I  S
                970                990                1010
GAAGAATTGGGCTTGAGTCTAGAAAACGCTGAAGTGGAGTTTTTAGGCAAAGCTGGAAGG
 E  E  L  G  L  S  L  E  N  A  E  V  E  F  L  G  K  A  G  R
                1030               1050               1070
ATTGTGATTGACAAAGACAACACCACGATCGTAGATGGCAAAGGCCATAGCGATGATGTT
 I  V  I  D  K  D  N  T  T  I  V  D  G  K  G  H  S  D  D  V
                1090               1110               1130
AAAGACAGAGTCGCGCAGATCAAAACCCAAATTGCAAGTACGACAAGCGATTATGACAAA
 K  D  R  V  A  Q  I  K  T  Q  I  A  S  T  T  S  D  Y  D  K
                1150               1170               1190
GAAAAATTGCAAGAAAGATTGGCTAAACTCTCTGGCGGTGTGGCTGTGATTAAAGTGGGC
 E  K  L  Q  E  R  L  A  K  L  S  G  G  V  A  V  I  K  V  G
                1210               1230               1250
GCTGCGAGTGAAGTGGAAATGAAAGAGAAAAAAGACCGGGTGGATGACGCGTTGAGCGCG
 A  A  S  E  V  E  M  K  E  K  K  D  R  V  D  D  A  L  S  A
                1270               1290               1310
ACTAAAGCGGCGGTTGAAGAAGGCATTGTGATTGGTGGCGGTGCGGCTCTCATTCGCGCG
 T  K  A  A  V  E  E  G  I  V  I  G  G  A  A  L  I  R  A
```

FIG. 5B

```
      1330              1350              1370
GCTCAAAAAGTGCATTTGAATTTGCACGATGATGAAAAAGTGGGCTATGAAATCATCATG
 A  Q  K  V  H  L  N  L  H  D  D  E  K  V  G  Y  E  I  I  M
      1390              1410              1430
CGCGCCATTAAAGCCCCATTAGCTCAAATCGCTATCAACGCTGGTTATGATGGCGGTGTG
 R  A  I  K  A  P  L  A  Q  I  A  I  N  A  G  Y  D  G  G  V
      1450              1470              1490
GTCGTGAATGAAGTAGAAAAACACGAAGGGCATTTTGGTTTTAACGCTAGCAATGGCAAG
 V  V  N  E  V  E  K  H  E  G  H  F  G  F  N  A  S  N  G  K
      1510              1530              1550
TATGTGGATATGTTTAAAGAAGGCATTATTGACCCCTTAAAAGTAGAAAGGATCGCTCTA
 Y  V  D  M  F  K  E  G  I  I  D  P  L  K  V  E  R  I  A  L
      1570              1590              1610
CAAAATGCGGTTTCGGTTTCAAGCCTGCTTTTAACCACAGAAGCCACCGTGCATGAAATC
 Q  N  A  V  S  V  S  S  L  L  L  T  T  E  A  T  V  H  E  I
      1630              1650              1670
AAAGAAGAAAAAGCGACTCCGGCAATGCCTGATATGGGTGGCATGGGCGGTATGGGAGGC
 K  E  E  K  A  T  P  A  M  P  D  M  G  G  M  G  G  M  G  G
      1690              1710              1730
ATGGGCGGCATGATGTAAGCCCGCTTGCTTTTAGTATAATCTGCTTTTAAAATCCCTTC
 M  G  G  M  M  *
      1750              1770              1790
TCTAAATCCCCCCCTTTCTAAAATCTCTTTTTTGGGGGGGTGCTTTGATAAAACCGCTCG
      1810              1830
CTTGTAAAAACATGCAACAAAAAATCTCTGTTAAGCTT
```

FIG. 5C

SEQUENCE LISTING

```
<160> NUMBER OF SEQ ID NOS: 30

<210> SEQ ID NO 1
<211> LENGTH: 27
<212> TYPE: DNA
<213> ORGANISM: Artificial Sequence
<220> FEATURE:
<223> OTHER INFORMATION: primer oligonucleotide

<400> SEQUENCE: 1
gcaagcttat cgatgtcgac tcgagct                                          27

<210> SEQ ID NO 2
<211> LENGTH: 3960
<212> TYPE: DNA
<213> ORGANISM: Helicobacter pylori

<400> SEQUENCE: 2 aaaagaaag gaagaaatg gaaatacaac aaacacaccg caaaatcaat cgccctctgg        60
tttctctcgc tttagtagga gcattagtca gcatcacacc gcaacaaagt catgccgcct     120
ttttcacaac cgtgatcatt ccagccattg ttgggggtat cgctacaggc accgctgtag     180
gaacggtctc agggcttctt agctgggggc tcaaacaagc cgaagaagcc aataaaaccc     240
cagataaacc cgataaagtt tggcgcattc aagcaggaaa aggctttaat gaattcccta     300
acaaggaata cgacttatac agatcccttt tatccagtaa gattgatgga ggttgggatt     360 ggggaatgc cgctaggcat tattgggtca aaggcgggca acagaataag cttgaagtgg     420
atatgaaaga cgctgtaggg acttatacct tatcagggct tagaaacttt actggtgggg     480
atttagatgt caatatgcaa aaagccactt tacgcttggg ccaattcaat ggcaattctt     540
ttacaagcta taaggatagt gctgatcgca ccacgagagt ggatttcaac gctaaaaata     600
tctcaattga taattttgta gaaatcaaca atcgtgtggg ttctggagcc gggaggaaag     660
ccagctctac ggttttgact ttgcaagctt cagaagggat cactagcgat aaaaacgctg     720
aaatttctct ttatgatggt gccacgctca atttggcttc aagcagcgtt aaattaatgg     780
gtaatgtgtg gatgggccgt ttgcaatacg tgggagcgta tttggccccct tcatacagca     840
```

```
cgataaacac ttcaaaagta acaggggaag tgaattttaa ccacctcact gttggcgata      900
aaaacgccgc tcaagcgggc attatcgcta ataaaaagac taatattggc acactggatt      960
tgtggcaaag cgccgggtta acattatcg ctcctccaga aggtggctat aaggataaac      1020
ccaataatac cccttctcaa agtggtgcta aaaacgacaa aatgaaagc gctaaaaacg       1080
acaaacaaga gagcagtcaa ataatagta acactcaggt cattaaccca cccaatagtg       1140
cgcaaaaaac agaagttcaa cccacgcaag tcattgatgg gccttttgcg ggcggcaaag      1200
acacggttgt caatatcaac cgcatcaaca ctaacgctga tggcacgatt agagtgggag      1260
ggtttaaagc ttctcttacc accaatgcgg ctcatttgca tatcggcaaa ggcggtgtca      1320
atctgtccaa tcaagcgagc gggcgctctc ttatagtgga aaatctaact gggaatatca      1380
ccgttgatgg gcctttaaga gtgaataatc aagtgggtgg ctatgctttg caggatcaa       1440
gcgcgaattt tgagtttaag gctggtacgg ataccaaaaa cggcacagcc acttttaata      1500
acgatattag tctgggaaga tttgtgaatt taaggtggaa tgctcataca gctaattta       1560
aaggtattga tacgggtaat ggtggttca acaccttaga ttttagtggc gttacagaca       1620
aagtcaatat caacaagctc attacggctt ccactaatgt ggccgttaaa aacttcaaca      1680
ttaatgaatt gattgttaaa accaatggga taagtgtggg ggaatatact cattttagcg      1740
aagatatagg cagtcaatcg cgcatcaata ccgtgcgttt ggaaactggc actaggtcac      1800
ttttctctgg gggtgttaaa tttaaaggtg gcgaaaaatt ggttatagat gagttttact      1860
atagcccttg gaattatttt gacgctagaa atattaaaaa tgttgaaatc accaataaac      1920
ttgcttttgg acctcaagga agtccttggg gcacatcaaa acttatgttc aataatctaa      1980
ccctaggtca aaatgcggtc atggattata gccaattttc aaatttaacc attcaagggg      2040
atttcatcaa caatcaaggc actatcaact atctggtccg aggtgggaaa gtggcaacct      2100
taagcgtagg caatgcagca gctatgatgt ttaataatga tatagacagc gcgaccggat      2160
tttacaaacc gctcatcaag attaacagcg ctcaagatct cattaaaaat acagaacatg      2220
ttttattgaa agcgaaaatc attggttatg gtaatgtttc tacaggtacc aatggcatta      2280
gtaatgttaa tctagaagag caattcaaag agcgcctagc cctttataac aacaataacc      2340
gcatggatac ttgtgtggtg cgaaatactg atgacattaa agcatgcggt atggctatcg      2400
gcgatcaaag catggtgaac aaccctgaca attacaagta tcttatcggt aaggcatgga      2460
aaaatatagg gatcagcaaa acagctaatg gctctaaaat ttcggtgtat tatttaggca      2520
attctacgcc tactgagaat ggtggcaata ccacaaattt acccacaaac accactagca      2580
atgcacgttc tgccaacaac gcccttgcac aaaacgctcc tttcgctcaa cctagtgcta      2640
ctcctaattt agtcgctatc aatcagcatg attttggcac tattgaaagc gtgtttgaat      2700
tggctaaccg ctctaaagat attgacacgc tttatgctaa ctcaggcgct caaggcaggg      2760
atctcttaca aaccttattg attgatagcc atgatgcggg ttatgccaga aaaatgattg      2820
atgctacaag cgctaatgaa atcaccaagc aattgaatac ggccactacc actttaaaca      2880
acatagccag tttagagcat aaaaccagcg gcttacaaac tttgagcttg agtaatgcga      2940
tgatttttaa ttctcgttta gtcaatctct ccaggagaca caccaaccat attgactcgt      3000
tcgccaaacg cttacaagct ttaaaagacc aaaaattcgc ttctttagaa agcgcggcag      3060
aagtgttgta tcaatttgcc cctaaatatg aaaaacctac caatgtttgg gctaacgcta      3120
ttgggggaac gagcttgaat aatggctcta acgcttcatt gtatggcaca agcgcgggcg      3180
tagacgctta ccttaacggg caagtggaag ccattgtggg cggttttgga agctatggtt      3240
```

-continued

```
atagctcttt taataatcgt gcgaactccc ttaactctgg ggccaataac actaattttg      3300
gcgtgtatag ccgtatttt gccaaccagc atgaatttga ctttgaagct caagggcac       3360 tagggagcga tcaatcaagc ttgaatttca aaagcgctct attacaagat ttgaatcaaa      3420
gctatcatta cttagcctat agcgctgcaa caagagcgag ctatggttat gacttcgcgt     3480
tttttaggaa cgctttagtg ttaaaaccaa gcgtgggtgt gagctataac catttaggtt     3540
caaccaactt taaaagcaac agcaccaatc aagtggcttt gaaaaatggc tctagcagtc     3600
agcatttatt caacgctagc gctaatgtgg aagcgcgcta ttattatggg gacacttcat     3660
acttctacat gaatgctgga gttttacaag agttcgctca tgttggctct aataacgccg     3720
cgtctttaaa cacctttaaa gtgaatgccg ctcgcaaccc tttaaatacc catgccagag     3780
tgatgatggg tggggaatta aaattagcta agaagtgtt tttgaatttg ggcgttgttt      3840
atttgcacaa tttgatttcc aatataggcc atttcgcttc caatttagga atgaggtata     3900
gtttctaaat accgctctta aacccatgct caaagcatgg gtttgaaatc ttacaaaaca     3960
```

<210> SEQ ID NO 3
<211> LENGTH: 1296
<212> TYPE: PRT
<213> ORGANISM: Helicobacter pylori

<400> SEQUENCE: 3

```
Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
            20                  25                  30

Ala Ala Phe Phe Thr Thr Val Ile Ile Pro Ala Ile Val Gly Gly Ile
        35                  40                  45

Ala Thr Gly Thr Ala Val Gly Thr Val Ser Gly Leu Leu Ser Trp Gly
    50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Arg Ser Leu Leu Ser Ser Lys Ile Asp Gly Gly
            100                 105                 110

Trp Asp Trp Gly Asn Ala Ala Arg His Tyr Trp Val Lys Gly Gly Gln
        115                 120                 125

Gln Asn Lys Leu Glu Val Asp Met Lys Asp Ala Val Gly Thr Tyr Thr
    130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
            180                 185                 190

Lys Asn Ile Ser Ile Asp Asn Phe Val Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Asp Lys Asn Ala Glu Ile Ser Leu Tyr Asp
225                 230                 235                 240

Gly Ala Thr Leu Asn Leu Ala Ser Ser Ser Val Lys Leu Met Gly Asn
```

-continued

```
                245                 250                 255
Val Trp Met Gly Arg Leu Gln Tyr Val Gly Ala Tyr Leu Ala Pro Ser
            260                 265                 270
Tyr Ser Thr Ile Asn Thr Ser Lys Val Thr Gly Glu Val Asn Phe Asn
        275                 280                 285
His Leu Thr Val Gly Asp Lys Asn Ala Ala Gln Ala Gly Ile Ile Ala
    290                 295                 300
Asn Lys Lys Thr Asn Ile Gly Thr Leu Asp Leu Trp Gln Ser Ala Gly
305                 310                 315                 320
Leu Asn Ile Ile Ala Pro Pro Glu Gly Gly Tyr Lys Asp Lys Pro Asn
                325                 330                 335
Asn Thr Pro Ser Gln Ser Gly Ala Lys Asn Asp Lys Asn Glu Ser Ala
            340                 345                 350
Lys Asn Asp Lys Gln Glu Ser Ser Gln Asn Asn Ser Asn Thr Gln Val
        355                 360                 365
Ile Asn Pro Pro Asn Ser Ala Gln Lys Thr Glu Val Gln Pro Thr Gln
    370                 375                 380
Val Ile Asp Gly Pro Phe Ala Gly Gly Lys Asp Thr Val Val Asn Ile
385                 390                 395                 400
Asn Arg Ile Asn Thr Asn Ala Asp Gly Thr Ile Arg Val Gly Gly Phe
                405                 410                 415
Lys Ala Ser Leu Thr Thr Asn Ala Ala His Leu His Ile Gly Lys Gly
            420                 425                 430
Gly Val Asn Leu Ser Asn Gln Ala Ser Gly Arg Ser Leu Ile Val Glu
        435                 440                 445
Asn Leu Thr Gly Asn Ile Thr Val Asp Gly Pro Leu Arg Val Asn Asn
    450                 455                 460
Gln Val Gly Gly Tyr Ala Leu Ala Gly Ser Ser Ala Asn Phe Glu Phe
465                 470                 475                 480
Lys Ala Gly Thr Asp Thr Lys Asn Gly Thr Ala Thr Phe Asn Asn Asp
                485                 490                 495
Ile Ser Leu Gly Arg Phe Val Asn Leu Lys Val Asp Ala His Thr Ala
            500                 505                 510
Asn Phe Lys Gly Ile Asp Thr Gly Asn Gly Phe Asn Thr Leu Asp
        515                 520                 525
Phe Ser Gly Val Thr Asp Lys Val Asn Ile Asn Lys Leu Ile Thr Ala
    530                 535                 540
Ser Thr Asn Val Ala Val Lys Asn Phe Asn Ile Asn Glu Leu Ile Val
545                 550                 555                 560
Lys Thr Asn Gly Ile Ser Val Gly Glu Tyr Thr His Phe Ser Glu Asp
                565                 570                 575
Ile Gly Ser Gln Ser Arg Ile Asn Thr Val Arg Leu Glu Thr Gly Thr
            580                 585                 590
Arg Ser Leu Phe Ser Gly Gly Val Lys Phe Lys Gly Gly Glu Lys Leu
        595                 600                 605
Val Ile Asp Glu Phe Tyr Tyr Ser Pro Trp Asn Tyr Phe Asp Ala Arg
    610                 615                 620
Asn Ile Lys Asn Val Glu Ile Thr Asn Lys Leu Ala Phe Gly Pro Gln
625                 630                 635                 640
Gly Ser Pro Trp Gly Thr Ser Lys Leu Met Phe Asn Asn Leu Thr Leu
                645                 650                 655
Gly Gln Asn Ala Val Met Asp Tyr Ser Gln Phe Ser Asn Leu Thr Ile
            660                 665                 670
```

-continued

Gln Gly Asp Phe Ile Asn Asn Gln Gly Thr Ile Asn Tyr Leu Val Arg
            675                 680                 685

Gly Gly Lys Val Ala Thr Leu Ser Val Gly Asn Ala Ala Met Met
        690                 695                 700

Phe Asn Asn Asp Ile Asp Ser Ala Thr Gly Phe Tyr Lys Pro Leu Ile
705                 710                 715                 720

Lys Ile Asn Ser Ala Gln Asp Leu Ile Lys Asn Thr Glu His Val Leu
            725                 730                 735

Leu Lys Ala Lys Ile Ile Gly Tyr Gly Asn Val Ser Thr Gly Thr Asn
        740                 745                 750

Gly Ile Ser Asn Val Asn Leu Glu Glu Gln Phe Lys Glu Arg Leu Ala
        755                 760                 765

Leu Tyr Asn Asn Asn Asn Arg Met Asp Thr Cys Val Val Arg Asn Thr
    770                 775                 780

Asp Asp Ile Lys Ala Cys Gly Met Ala Ile Gly Asp Gln Ser Met Val
785                 790                 795                 800

Asn Asn Pro Asp Asn Tyr Lys Tyr Leu Ile Gly Lys Ala Trp Lys Asn
            805                 810                 815

Ile Gly Ile Ser Lys Thr Ala Asn Gly Ser Lys Ile Ser Val Tyr Tyr
        820                 825                 830

Leu Gly Asn Ser Thr Pro Thr Glu Asn Gly Gly Asn Thr Thr Asn Leu
        835                 840                 845

Pro Thr Asn Thr Thr Ser Asn Ala Arg Ser Ala Asn Asn Ala Leu Ala
    850                 855                 860

Gln Asn Ala Pro Phe Ala Gln Pro Ser Ala Thr Pro Asn Leu Val Ala
865                 870                 875                 880

Ile Asn Gln His Asp Phe Gly Thr Ile Glu Ser Val Phe Glu Leu Ala
            885                 890                 895

Asn Arg Ser Lys Asp Ile Asp Thr Leu Tyr Ala Asn Ser Gly Ala Gln
            900                 905                 910

Gly Arg Asp Leu Leu Gln Thr Leu Leu Ile Asp Ser His Asp Ala Gly
        915                 920                 925

Tyr Ala Arg Lys Met Ile Asp Ala Thr Ser Ala Asn Glu Ile Thr Lys
    930                 935                 940

Gln Leu Asn Thr Ala Thr Thr Leu Asn Asn Ile Ala Ser Leu Glu
945                 950                 955                 960

His Lys Thr Ser Gly Leu Gln Thr Leu Ser Leu Ser Asn Ala Met Ile
            965                 970                 975

Leu Asn Ser Arg Leu Val Asn Leu Ser Arg Arg His Thr Asn His Ile
            980                 985                 990

Asp Ser Phe Ala Lys Arg Leu Gln Ala Leu Lys Asp Gln Lys Phe Ala
        995                 1000                1005

Ser Leu Glu Ser Ala Ala Glu Val Leu Tyr Gln Phe Ala Pro Lys
    1010                1015                1020

Tyr Glu Lys Pro Thr Asn Val Trp Ala Asn Ala Ile Gly Gly Thr
    1025                1030                1035

Ser Leu Asn Asn Gly Ser Asn Ala Ser Leu Tyr Gly Thr Ser Ala
    1040                1045                1050

Gly Val Asp Ala Tyr Leu Asn Gly Gln Val Glu Ala Ile Val Gly
    1055                1060                1065

Gly Phe Gly Ser Tyr Gly Tyr Ser Ser Phe Asn Asn Arg Ala Asn
    1070                1075                1080

-continued

| | | | | | | | | | | |
|---|---|---|---|---|---|---|---|---|---|---|
| Ser | Leu | Asn | Ser | Gly | Ala | Asn | Asn | Thr | Asn | Phe | Gly | Val | Tyr | Ser |
| | 1085 | | | | 1090 | | | | 1095 | |
| Arg | Ile | Phe | Ala | Asn | Gln | His | Glu | Phe | Asp | Phe | Glu | Ala | Gln | Gly |
| | 1100 | | | | 1105 | | | | 1110 | |
| Ala | Leu | Gly | Ser | Asp | Gln | Ser | Ser | Leu | Asn | Phe | Lys | Ser | Ala | Leu |
| | 1115 | | | | 1120 | | | | 1125 | |
| Leu | Gln | Asp | Leu | Asn | Gln | Ser | Tyr | His | Tyr | Leu | Ala | Tyr | Ser | Ala |
| | 1130 | | | | 1135 | | | | 1140 | |
| Ala | Thr | Arg | Ala | Ser | Tyr | Gly | Tyr | Asp | Phe | Ala | Phe | Phe | Arg | Asn |
| | 1145 | | | | 1150 | | | | 1155 | |
| Ala | Leu | Val | Leu | Lys | Pro | Ser | Val | Gly | Val | Ser | Tyr | Asn | His | Leu |
| | 1160 | | | | 1165 | | | | 1170 | |
| Gly | Ser | Thr | Asn | Phe | Lys | Ser | Asn | Ser | Thr | Asn | Gln | Val | Ala | Leu |
| | 1175 | | | | 1180 | | | | 1185 | |
| Lys | Asn | Gly | Ser | Ser | Ser | Gln | His | Leu | Phe | Asn | Ala | Ser | Ala | Asn |
| | 1190 | | | | 1195 | | | | 1200 | |
| Val | Glu | Ala | Arg | Tyr | Tyr | Tyr | Gly | Asp | Thr | Ser | Tyr | Phe | Tyr | Met |
| | 1205 | | | | 1210 | | | | 1215 | |
| Asn | Ala | Gly | Val | Leu | Gln | Glu | Phe | Ala | His | Val | Gly | Ser | Asn | Asn |
| | 1220 | | | | 1225 | | | | 1230 | |
| Ala | Ala | Ser | Leu | Asn | Thr | Phe | Lys | Val | Asn | Ala | Ala | Arg | Asn | Pro |
| | 1235 | | | | 1240 | | | | 1245 | |
| Leu | Asn | Thr | His | Ala | Arg | Val | Met | Met | Gly | Gly | Glu | Leu | Lys | Leu |
| | 1250 | | | | 1255 | | | | 1260 | |
| Ala | Lys | Glu | Val | Phe | Leu | Asn | Leu | Gly | Val | Val | Tyr | Leu | His | Asn |
| | 1265 | | | | 1270 | | | | 1275 | |
| Leu | Ile | Ser | Asn | Ile | Gly | His | Phe | Ala | Ser | Asn | Leu | Gly | Met | Arg |
| | 1280 | | | | 1285 | | | | 1290 | |
| Tyr | Ser | Phe |
| | 1295 | |

<210> SEQ ID NO 4
<211> LENGTH: 5925
<212> TYPE: DNA
<213> ORGANISM: Helicobacter pylori

<400> SEQUENCE: 4

```
ctccatttta agcaactcca tagaccacta aagaaacttt ttttgaggct atctttgaaa    60
atctgtccta ttgatttgtt ttccattttg tttcccatgt ggatcttgtg gatcacaaac   120
gcttaattat acatgctata gtaagcatga cacacaaacc aaactatttt tagaacgctt   180
catgtgctca ccttgactaa ccatttctcc aaccatactt tagcgttgca tttgatttct   240
tcaaaagat tcatttctta tttcttgttc ttattaaagt tctttcattt tagcaaattt    300
ttgttaattg tgggtaaaaa tgtgaatcgt cctagccttt agacgcctgc aacgatcggg   360
cttttttcaa tattaataat gattaatgaa aaaaaaaaaa aatgcttgat attgttgtat   420
aatgagaatg ttcaaagaca tgaattgact actcaagcgt gtagcgattt ttagcagtct   480
ttgacactaa caagataccg ataggtatga aactaggtat agtaaggaga acaatgact    540
aacgaaacca ttgaccaaca accacaaacc gaagcggctt taacccgca gcaatttatc    600
aataatcttc aagtagcttt tcttaaagtt gataacgctg tcgcttcata cgatcctgat   660
caaaaaccaa tcgttgataa gaacgatagg gataacaggc aagctttga aggaatctcg    720
caattaaggg aagaatactc caataaagcg atcaaaaatc ctaccaaaaa gaatcagtat   780
```

-continued

```
ttttcagact ttatcaataa gagcaatgat ttaatcaaca aagacaatct cattgatgta      840
gaatcttcca caaagagctt tcagaaattt ggggatcagc gttaccgaat tttcacaagt      900
tgggtgtccc atcaaaacga tccgtctaaa atcaacaccc gatcgatccg aaattttatg      960
gaaaatatca tacaaccccc tatccttgat gataaagaga aagcggagtt tttgaaatct     1020
gccaaacaat cttttgcagg aatcattata gggaatcaaa tccgaacgga tcaaaagttc     1080
atgggcgtgt tgatgagtc cttgaaagaa aggcaagaag cagaaaaaaa tggagagcct     1140
actggtgggg attggttgga tattttctc tcatttatat ttgacaaaaa acaatcttct     1200
gatgtcaaag aagcaatcaa tcaagaacca gttccccatg tccaaccaga tatagccact     1260
accaccaccg acatacaagg cttaccgcct gaagctagag atttacttga tgaaaggggt     1320
aatttttcta aattcactct tggcgatatg gaaatgttag atgttgaggg agtcgctgac     1380
attgatccca attacaagtt caatcaatta ttgattcaca ataacgctct gtcttctgtg     1440
ttaatgggga gtcataatgg catagaacct gaaaaagttt cattgttgta tgggggcaat     1500
ggtggtcctg gagctaggca tgattggaac gccaccgttg gttataaaga ccaacaaggc     1560
aacaatgtgg ctacaataat taatgtgcat atgaaaaacg gcagtggctt agtcatagca     1620
ggtggtgaga aagggattaa caaccctagt ttttatctct acaaagaaga ccaactcaca     1680
ggctcacaac gagcattaag tcaagaagag atccaaaaca aaatagattt catgaaattt     1740
cttgcacaaa ataatgctaa attagacaac ttgagcgaga agagaagga aaaattccga     1800 actgagatta aagatttcca aaaagactct aaggcttatt tagacgccct agggaatgat     1860
cgtattgctt ttgtttctaa aaaagacaca aaacattcag ctttaattac tgagtttggt     1920 aatgggatt tgagctacac tctcaaagat tatgggaaaa aagcagataa agctttagat     1980
agggagaaaa atgttactct tcaaggtagc ctaaaacatg atggcgtgat gtttgttgat     2040
tattctaatt tcaaatacac caacgcctcc aagaatccca ataagggtgt aggcgttacg     2100
aatggcgttt cccatttaga agtaggcttt aacaaggtag ctatctttaa tttgcctgat     2160
ttaaataatc tcgctatcac tagtttcgta aggcggaatt tagaggataa actaaccact     2220
aaaggattgt ccccacaaga agctaataag cttatcaaag attttttgag cagcaacaaa     2280
gaattggttg gaaaaacttt aaacttcaat aaagctgtag ctgacgctaa aaacacaggc     2340
aattatgatg aagtgaaaaa agctcagaaa gatcttgaaa aatctctaag gaaacgagag     2400
catttagaga aagaagtaga gaaaaaattg gagagcaaaa gcggcaacaa aaataaaatg     2460
gaagcaaaag ctcaagctaa cagccaaaaa gatgagattt ttgcgttgat caataaaag     2520 gctaatagag acgcaagagc aatcgcttac gctcagaatc ttaaaggcat caaaagggaa     2580
ttgtctgata aacttgaaaa tgtcaacaag aatttgaaag actttgataa atcttttgat     2640
gaattcaaaa atggcaaaaa taaggatttc agcaaggcag aagaaacact aaaagcccctt     2700 aaaggttcgg tgaaagattt aggtatcaat ccagaatgga tttcaaagt tgaaaacctt     2760 aatgcagctt tgaatgaatt caaaatggc aaaaataagg atttcagcaa ggtaacgcaa     2820
gcaaaaagcg accttgaaaa ttccgttaaa gatgtgatca tcaatcaaaa ggtaacggat     2880
aaagttgata atctcaatca agcggtatca gtggctaaag caacgggtga tttcagtagg     2940
gtagagcaag cgttagccga tctcaaaaat ttctcaaagg agcaattggc ccaacaagct     3000 caaaaaatg aaagtctcaa tgctagaaaa aaatctgaaa tatatcaatc cgttaagaat     3060
ggtgtgaatg gaaccctagt cggtaatggg ttatctcaag cagaagccac aactctttct     3120 aaaaacttt cggacatcaa gaaagagttg aatgcaaaac ttggaaattt caataacaat     3180
```

```
aacaataatg gactcaaaaa cgaacccatt tatgctaaag ttaataaaaa gaaagcaggg    3240
caagcagcta gccttgaaga acccatttac gctcaagttg ctaaaaaggt aaatgcaaaa    3300
attgaccgac tcaatcaaat agcaagtggt ttgggtgttg tagggcaagc agcgggcttc    3360
cctttgaaaa ggcatgataa agttgatgat ctcagtaagg tagggctttc aaggaatcaa    3420
gaattggctc agaaaattga caatctcaat caagcggtat cagaagctaa agcaggtttt    3480
tttggcaatc tagagcaaac gatagacaag ctcaaagatt ctacaaaaca caatcccatg    3540
aatctatggg ttgaaagtgc aaaaaaagta cctgctagtt tgtcagcgaa actagacaat    3600
tacgctacta acagccacat acgcattaat agcaatatca aaaatggagc aatcaatgaa    3660
aaagcgaccg gcatgctaac gcaaaaaaac cctgagtggc tcaagctcgt gaatgataag    3720
atagttgcgc ataatgtagg aagcgttcct ttgtcagagt atgataaaat tggcttcaac    3780
cagaagaata tgaaagatta ttctgattcg ttcaagtttt ccaccaagtt gaacaatgct    3840
gtaaaagaca ctaattctgg ctttacgcaa tttttaacca atgcattttc tacagcatct    3900
tattactgct tggcgagaga aaatgcggag catggaatca agaacgttaa tacaaaaggt    3960
ggtttccaaa aatcttaaag gattaaggaa taccaaaaac gcaaaaacca cccctttgcta   4020 aaagcgaggg gttttttaat actccttagc agaaatccca atcgtcttta gtatttggga    4080
tgaatgctac caattcatgg tatcatatcc ccatacattc gtatctagcg taggaagtgt    4140
gcaaagttac gccttggag atatgatgtg tgagacctgt agggaatgcg ttggagctca     4200
aactctgtaa aatccctatt atagggacac agagtgagaa ccaaactctc cctacgggca    4260
acatcagcct aggaagccca atcgtcttta gcggttgggc acttcacctt aaaatatccc    4320
gacagacact aacgaaaggc tttgttcttt aaagtctgca tggatatttc ctaccccaaa    4380
aagacttaac cctttgctta aaattaagtt tgattgtgct agtgggttcg tgctatagtg    4440
cgaaaattaa ttaagggtta taagagagc ataaactaga aaaacaagt agctataaca     4500 aagatcaagt tcaaaaaatc atagagcttt tagagcaaat tgatcgcgct cttaaccaaa    4560
gaaaaatcag aaaaaccata ggaattatca caccttataa tgcccaaaaa agacgcttgc    4620
gatcagaagt ggaaaaatac ggcttcaaga attttgatga gctcaaaata gacactgtgg    4680 atgccttca aggtgaagag gcagatatta ttatttattc caccgtgaaa acttgtggta     4740
atctttcttt cttgctagat tctaaacgct tgaatgtggc tatttctagg gcaaaagaaa    4800
atctcatttt tgtgggtaaa aagtcttcct ttgagaattt atgaagcgat gagaagaata    4860
tctttagcgc tattttgcaa gtctgtagat aggtaatctt ttccaaagat aatcattaga    4920
cattcttcgc ttcaaaacgc tttcataaat ctctctaaag cgctttataa tcaacacaat    4980
acccttatag tgtgagctat agccccttt tgggaattga gttattttga ctttaaattt     5040
ttattagcgt tacaatttga gccattcttt agcttgtttt tctagccaga tcacatcgcc    5100
gctcgcatga aattccactt tagggaatgc gtgtgcattt tttttaaggg cgtattttg     5160 ctgcaaatat cctacaatag catcgcccga atggatgagt agggggggtg ttgaaagggc    5220
aaaatgctcc ataaaatagc cctcaatttt ttgagcgatt aagggaaaat gcgtgcaacc    5280
taaaataatc acttcgggaa aatctttaag ggagtgaaat aataacgcat gcaagtttct    5340
aacaattcgc cctctaaaat actttcttca atcaaaggca caaaagaga agtggctaaa    5400 tgcgaaacat tcaaatagcc ttgttgtttc agggcattgt cataagcgtt ggattggatc    5460
gtcgcttttg tccctagcac taaaataggg gcgtttttat cttttacttg tcgcttgatc    5520
```

-continued

```
gctaaaatgc ttggctcaat cacgcccaca atagggattt tggaatgctt ttgcatctct    5580
tctaaagcta gagcgctcgc tgtgttgcat gccacaatca ataattcaat ctggtgcggt    5640
ttgaaaaaat ccaaagcctc taagccaaat tgcttgatcg tagtggggtc tttagtgcca    5700
taaggcactc tagccgtatc gccataatag atgatttcat caaataattg cgcttttaaa    5760 aggctttttta aaacgctaaa ccctcccaca ccgctatcaa aaacgcctat tttcatgaca    5820
cttttttaat ttaatgggat taattaggga ttttattttt cattcattaa gtttaaaaat    5880
tcttcattgt ccttagtttg ttgcatttta gaatagacaa agctt                    5925
```

<210> SEQ ID NO 5
<211> LENGTH: 1147
<212> TYPE: PRT
<213> ORGANISM: Helicobacter pylori
<400> SEQUENCE: 5

```
Met Thr Asn Glu Thr Ile Asp Gln Gln Pro Gln Thr Glu Ala Ala Phe
1               5                   10                  15

Asn Pro Gln Gln Phe Ile Asn Asn Leu Gln Val Ala Phe Leu Lys Val
            20                  25                  30

Asp Asn Ala Val Ala Ser Tyr Asp Pro Asp Gln Lys Pro Ile Val Asp
        35                  40                  45

Lys Asn Asp Arg Asp Asn Arg Gln Ala Phe Glu Gly Ile Ser Gln Leu
    50                  55                  60

Arg Glu Glu Tyr Ser Asn Lys Ala Ile Lys Asn Pro Thr Lys Lys Asn
65                  70                  75                  80

Gln Tyr Phe Ser Asp Phe Ile Asn Lys Ser Asn Asp Leu Ile Asn Lys
                85                  90                  95

Asp Asn Leu Ile Asp Val Glu Ser Ser Thr Lys Ser Phe Gln Lys Phe
            100                 105                 110

Gly Asp Gln Arg Tyr Arg Ile Phe Thr Ser Trp Val Ser His Gln Asn
        115                 120                 125

Asp Pro Ser Lys Ile Asn Thr Arg Ser Ile Arg Asn Phe Met Glu Asn
    130                 135                 140

Ile Ile Gln Pro Pro Ile Leu Asp Asp Lys Glu Lys Ala Glu Phe Leu
145                 150                 155                 160

Lys Ser Ala Lys Gln Ser Phe Ala Gly Ile Ile Gly Asn Gln Ile
                165                 170                 175

Arg Thr Asp Gln Lys Phe Met Gly Val Phe Asp Glu Ser Leu Lys Glu
            180                 185                 190

Arg Gln Glu Ala Glu Lys Asn Gly Glu Pro Thr Gly Gly Asp Trp Leu
        195                 200                 205

Asp Ile Phe Leu Ser Phe Ile Phe Asp Lys Lys Gln Ser Ser Asp Val
    210                 215                 220

Lys Glu Ala Ile Asn Gln Glu Pro Val Pro His Val Gln Pro Asp Ile
225                 230                 235                 240

Ala Thr Thr Thr Thr Asp Ile Gln Gly Leu Pro Pro Glu Ala Arg Asp
                245                 250                 255

Leu Leu Asp Glu Arg Gly Asn Phe Ser Lys Phe Thr Leu Gly Asp Met
            260                 265                 270

Glu Met Leu Asp Val Glu Gly Val Ala Asp Ile Asp Pro Asn Tyr Lys
        275                 280                 285

Phe Asn Gln Leu Leu Ile His Asn Asn Ala Leu Ser Ser Val Leu Met
    290                 295                 300
```

-continued

```
Gly Ser His Asn Gly Ile Glu Pro Glu Lys Val Ser Leu Leu Tyr Gly
305                 310                 315                 320

Gly Asn Gly Gly Pro Gly Ala Arg His Asp Trp Asn Ala Thr Val Gly
            325                 330                 335

Tyr Lys Asp Gln Gln Gly Asn Asn Val Ala Thr Ile Ile Asn Val His
        340                 345                 350

Met Lys Asn Gly Ser Gly Leu Val Ile Ala Gly Gly Glu Lys Gly Ile
    355                 360                 365

Asn Asn Pro Ser Phe Tyr Leu Tyr Lys Glu Asp Gln Leu Thr Gly Ser
370                 375                 380

Gln Arg Ala Leu Ser Gln Glu Ile Gln Asn Lys Ile Asp Phe Met
385                 390                 395                 400

Glu Phe Leu Ala Gln Asn Ala Lys Leu Asp Asn Leu Ser Glu Lys
                405                 410                 415

Glu Lys Glu Lys Phe Arg Thr Glu Ile Lys Asp Phe Gln Lys Asp Ser
            420                 425                 430

Lys Ala Tyr Leu Asp Ala Leu Gly Asn Asp Arg Ile Ala Phe Val Ser
        435                 440                 445

Lys Lys Asp Thr Lys His Ser Ala Leu Ile Thr Glu Phe Gly Asn Gly
    450                 455                 460

Asp Leu Ser Tyr Thr Leu Lys Asp Tyr Gly Lys Lys Ala Asp Lys Ala
465                 470                 475                 480

Leu Asp Arg Glu Lys Asn Val Thr Leu Gln Gly Ser Leu Lys His Asp
                485                 490                 495

Gly Val Met Phe Val Asp Tyr Ser Asn Phe Lys Tyr Thr Asn Ala Ser
            500                 505                 510

Lys Asn Pro Asn Lys Gly Val Gly Val Thr Asn Gly Val Ser His Leu
        515                 520                 525

Glu Val Gly Phe Asn Lys Val Ala Ile Phe Asn Leu Pro Asp Leu Asn
    530                 535                 540

Asn Leu Ala Ile Thr Ser Phe Val Arg Arg Asn Leu Glu Asp Lys Leu
545                 550                 555                 560

Thr Thr Lys Gly Leu Ser Pro Gln Glu Ala Asn Lys Leu Ile Lys Asp
                565                 570                 575

Phe Leu Ser Ser Asn Lys Glu Leu Val Gly Lys Thr Leu Asn Phe Asn
            580                 585                 590

Lys Ala Val Ala Asp Ala Lys Asn Thr Gly Asn Tyr Asp Glu Val Lys
        595                 600                 605

Lys Ala Gln Lys Asp Leu Glu Lys Ser Leu Arg Lys Arg Glu His Leu
    610                 615                 620

Glu Lys Glu Val Glu Lys Leu Glu Ser Lys Ser Gly Asn Lys Asn
625                 630                 635                 640

Lys Met Glu Ala Lys Ala Gln Ala Asn Ser Gln Lys Asp Glu Ile Phe
                645                 650                 655

Ala Leu Ile Asn Lys Glu Ala Asn Arg Asp Ala Arg Ala Ile Ala Tyr
            660                 665                 670

Ala Gln Asn Leu Lys Gly Ile Lys Arg Glu Leu Ser Asp Lys Leu Glu
        675                 680                 685

Asn Val Asn Lys Asn Leu Lys Asp Phe Asp Lys Ser Phe Asp Glu Phe
    690                 695                 700

Lys Asn Gly Lys Asn Lys Asp Phe Ser Lys Ala Glu Glu Thr Leu Lys
705                 710                 715                 720

Ala Leu Lys Gly Ser Val Lys Asp Leu Gly Ile Asn Pro Glu Trp Ile
```

-continued

```
                725                 730                 735
Ser Lys Val Glu Asn Leu Asn Ala Ala Leu Asn Glu Phe Lys Asn Gly
            740                 745                 750
Lys Asn Lys Asp Phe Ser Lys Val Thr Gln Ala Lys Ser Asp Leu Glu
            755                 760                 765
Asn Ser Val Lys Asp Val Ile Ile Asn Gln Lys Val Thr Asp Lys Val
            770                 775                 780
Asp Asn Leu Asn Gln Ala Val Ser Val Ala Lys Ala Thr Gly Asp Phe
785                 790                 795                 800
Ser Arg Val Glu Gln Ala Leu Ala Asp Leu Lys Asn Phe Ser Lys Glu
            805                 810                 815
Gln Leu Ala Gln Gln Ala Gln Lys Asn Glu Ser Leu Asn Ala Arg Lys
            820                 825                 830
Lys Ser Glu Ile Tyr Gln Ser Val Lys Asn Gly Val Asn Gly Thr Leu
            835                 840                 845
Val Gly Asn Gly Leu Ser Gln Ala Glu Ala Thr Thr Leu Ser Lys Asn
            850                 855                 860
Phe Ser Asp Ile Lys Lys Glu Leu Asn Ala Lys Leu Gly Asn Phe Asn
865                 870                 875                 880
Asn Asn Asn Asn Asn Gly Leu Lys Asn Glu Pro Ile Tyr Ala Lys Val
                    885                 890                 895
Asn Lys Lys Lys Ala Gly Gln Ala Ala Ser Leu Glu Glu Pro Ile Tyr
            900                 905                 910
Ala Gln Val Ala Lys Lys Val Asn Ala Lys Ile Asp Arg Leu Asn Gln
            915                 920                 925
Ile Ala Ser Gly Leu Gly Val Val Gly Gln Ala Ala Gly Phe Pro Leu
            930                 935                 940
Lys Arg His Asp Lys Val Asp Asp Leu Ser Lys Val Gly Leu Ser Arg
945                 950                 955                 960
Asn Gln Glu Leu Ala Gln Lys Ile Asp Asn Leu Asn Gln Ala Val Ser
                    965                 970                 975
Glu Ala Lys Ala Gly Phe Phe Gly Asn Leu Glu Gln Thr Ile Asp Lys
            980                 985                 990
Leu Lys Asp Ser Thr Lys His Asn  Pro Met Asn Leu Trp  Val Glu Ser
            995                 1000                1005
Ala Lys  Lys Val Pro Ala Ser  Leu Ser Ala Lys Leu  Asp Asn Tyr
 1010                1015                1020
Ala Thr  Asn Ser His Ile Arg  Ile Asn Ser Asn Ile  Lys Asn Gly
 1025                1030                1035
Ala Ile  Asn Glu Lys Ala Thr  Gly Met Leu Thr Gln  Lys Asn Pro
 1040                1045                1050
Glu Trp  Leu Lys Leu Val Asn  Asp Lys Ile Val Ala  His Asn Val
 1055                1060                1065
Gly Ser  Val Pro Leu Ser Glu  Tyr Asp Lys Ile Gly  Phe Asn Gln
 1070                1075                1080
Lys Asn  Met Lys Asp Tyr Ser  Asp Ser Phe Lys Phe  Ser Thr Lys
 1085                1090                1095
Leu Asn  Asn Ala Val Lys Asp  Thr Asn Ser Gly Phe  Thr Gln Phe
 1100                1105                1110
Leu Thr  Asn Ala Phe Ser Thr  Ala Ser Tyr Tyr Cys  Leu Ala Arg
 1115                1120                1125
Glu Asn  Ala Glu His Gly Ile  Lys Asn Val Asn Thr  Lys Gly Gly
 1130                1135                1140
```

Phe Gln  Lys Ser
   1145

<210> SEQ ID NO 6
<211> LENGTH: 546
<212> TYPE: PRT
<213> ORGANISM: Helicobacter pylori

<400> SEQUENCE: 6

| Met | Ala | Lys | Glu | Ile | Lys | Phe | Ser | Asp | Ser | Ala | Arg | Asn | Leu | Leu | Phe |
|-----|-----|-----|-----|-----|-----|-----|-----|-----|-----|-----|-----|-----|-----|-----|-----|
| 1 | | | | 5 | | | | | 10 | | | | | 15 | |

Glu Gly Val Arg Gln Leu His Asp Ala Val Lys Val Thr Met Gly Pro
            20                  25                  30

Arg Gly Arg Asn Val Leu Ile Gln Lys Ser Tyr Gly Ala Pro Ser Ile
        35                  40                  45

Thr Lys Asp Gly Val Ser Val Ala Lys Glu Ile Glu Leu Ser Cys Pro
 50                  55                  60

Val Ala Asn Met Gly Ala Gln Leu Val Lys Glu Val Ala Ser Lys Thr
 65                  70                  75                  80

Ala Asp Ala Ala Gly Asp Gly Thr Thr Thr Ala Thr Val Leu Ala Tyr
                85                  90                  95

Ser Ile Phe Lys Glu Gly Leu Arg Asn Ile Thr Ala Gly Ala Asn Pro
            100                 105                 110

Ile Glu Val Lys Arg Gly Met Asp Lys Ala Ala Glu Ala Ile Ile Asn
        115                 120                 125

Glu Leu Lys Lys Ala Ser Lys Lys Val Gly Gly Lys Glu Glu Ile Thr
130                 135                 140

Gln Val Ala Thr Ile Ser Ala Asn Ser Asp His Asn Ile Gly Lys Leu
145                 150                 155                 160

Ile Ala Asp Ala Met Glu Lys Val Gly Lys Asp Gly Val Ile Thr Val
                165                 170                 175

Glu Glu Ala Lys Gly Ile Glu Asp Glu Leu Asp Val Val Glu Gly Met
            180                 185                 190

Gln Phe Asp Arg Gly Tyr Leu Ser Pro Tyr Phe Val Thr Asn Ala Glu
        195                 200                 205

Lys Met Thr Ala Gln Leu Asp Asn Ala Tyr Ile Leu Leu Thr Asp Lys
210                 215                 220

Lys Ile Ser Ser Met Lys Asp Ile Leu Pro Leu Leu Glu Lys Thr Met
225                 230                 235                 240

Lys Glu Gly Lys Pro Leu Leu Ile Ile Ala Glu Asp Ile Glu Gly Glu
                245                 250                 255

Ala Leu Thr Thr Leu Val Val Asn Lys Leu Arg Gly Val Leu Asn Ile
            260                 265                 270

Ala Ala Val Lys Ala Pro Gly Phe Gly Asp Arg Arg Lys Glu Met Leu
        275                 280                 285

Lys Asp Ile Ala Ile Leu Thr Gly Gly Gln Val Ile Ser Glu Glu Leu
290                 295                 300

Gly Leu Ser Leu Glu Asn Ala Glu Val Glu Phe Leu Gly Lys Ala Gly
305                 310                 315                 320

Arg Ile Val Ile Asp Lys Asp Asn Thr Thr Ile Val Asp Gly Lys Gly
                325                 330                 335

His Ser Asp Asp Val Lys Asp Arg Val Ala Gln Ile Lys Thr Gln Ile
            340                 345                 350

Ala Ser Thr Thr Ser Asp Tyr Asp Lys Glu Lys Leu Gln Glu Arg Leu

-continued

```
                    355                 360                 365
Ala Lys Leu Ser Gly Gly Val Ala Val Ile Lys Val Gly Ala Ala Ser
        370                 375                 380
Glu Val Glu Met Lys Glu Lys Lys Asp Arg Val Asp Asp Ala Leu Ser
385                 390                 395                 400
Ala Thr Lys Ala Ala Val Glu Glu Gly Ile Val Ile Gly Gly Gly Ala
                405                 410                 415
Ala Leu Ile Arg Ala Ala Gln Lys Val His Leu Asn Leu His Asp Asp
            420                 425                 430
Glu Lys Val Gly Tyr Glu Ile Ile Met Arg Ala Ile Lys Ala Pro Leu
        435                 440                 445
Ala Gln Ile Ala Ile Asn Ala Gly Tyr Asp Gly Gly Val Val Val Asn
    450                 455                 460
Glu Val Glu Lys His Glu Gly His Phe Gly Phe Asn Ala Ser Asn Gly
465                 470                 475                 480
Lys Tyr Val Asp Met Phe Lys Glu Gly Ile Ile Asp Pro Leu Lys Val
                485                 490                 495
Glu Arg Ile Ala Leu Gln Asn Ala Val Ser Val Ser Ser Leu Leu Leu
            500                 505                 510
Thr Thr Glu Ala Thr Val His Glu Ile Lys Glu Glu Lys Ala Thr Pro
        515                 520                 525
Ala Met Pro Asp Met Gly Gly Met Gly Gly Met Gly Gly Met Gly Gly
    530                 535                 540
Met Met
545
```

<210> SEQ ID NO 7
<211> LENGTH: 1838
<212> TYPE: DNA
<213> ORGANISM: Helicobacter pylori

<400> SEQUENCE: 7

| | | | | |
|---|---|---|---|---|
| aagcttgctg | tcatgatcac | aaaaaacact | aaaaaacatt | attattaagg | atacaaaatg | 60 |
| gcaaaagaaa | tcaaattttc | agatagtgcg | agaaaccttt | tatttgaagg | cgtgaggcaa | 120 |
| ctccatgacg | ctgtcaaagt | aaccatgggg | ccaagaggca | ggaatgtatt | gatccaaaaa | 180 |
| agctatggcg | ctccaagcat | caccaaagac | ggcgtgagcg | tggctaaaga | gattgaatta | 240 |
| agttgcccag | tagctaacat | gggcgctcaa | ctcgttaaag | aagtagcgag | caaaaccgct | 300 |
| gatgctgccg | gcgatggcac | gaccacagcg | accgtgctag | cttatagcat | ttttaaagaa | 360 |
| ggtttgagga | atatcacggc | tggggctaac | cctattgaag | tgaaacgagg | catggataaa | 420 |
| gctgctgaag | cgatcattaa | tgagcttaaa | aaagcgagca | aaaagtagg | cggtaaagaa | 480 |
| gaaatcaccc | aagtggcgac | catttctgca | aactccgatc | acaatatcgg | gaaactcatc | 540 |
| gctgacgcta | tggaaaaagt | gggtaaagac | ggcgtgatca | ccgttgagga | agctaagggc | 600 |
| attgaagatg | aattggatgt | cgtagaaggc | atgcaatttg | atagaggcta | cctctcccct | 660 |
| tattttgtaa | cgaacgctga | gaaaatgacc | gctcaattgg | ataatgctta | catcctttta | 720 |
| acggataaaa | aaatctctag | catgaaagac | attctcccgc | tactagaaaa | aaccatgaaa | 780 |
| gagggcaaac | cgcttttaat | catcgctgaa | gacattgagg | cgaagcttt | aacgactcta | 840 |
| gtggtgaata | attaagagg | cgtgttgaat | atcgcagcgg | ttaaagctcc | aggctttggg | 900 |
| gacagaagaa | aagaaatgct | caagacatc | gctattttaa | ccggcggtca | agtcattagc | 960 |
| gaagaattgg | gcttgagtct | agaaaacgct | gaagtggagt | ttttaggcaa | agctggaagg | 1020 |

-continued

```
attgtgattg acaaagacaa caccacgatc gtagatggca aaggccatag cgatgatgtt    1080
aaagacagag tcgcgcagat caaaacccaa attgcaagta cgacaagcga ttatgacaaa    1140
gaaaaattgc aagaaagatt ggctaaactc tctggcggtg tggctgtgat taaagtgggc    1200
gctgcgagtg aagtggaaat gaaagagaaa aaagaccggg tggatgacgc gttgagcgcg    1260
actaaagcgg cggttgaaga aggcattgtg attggtggcg gtgcggctct cattcgcgcg    1320
gctcaaaaag tgcatttgaa tttgcacgat gatgaaaaag tgggctatga atcatcatg     1380 cgcgccatta agcccccatt agctcaaatc gctatcaacg ctggttatga tggcggtgtg    1440
gtcgtgaatg aagtagaaaa acacgaaggg catttggtt ttaacgctag caatggcaag     1500
tatgtggata tgtttaaaga aggcattatt gaccccttaa aagtagaaag gatcgctcta    1560
caaaatgcgg tttcggtttc aagcctgctt ttaaccacag aagccaccgt gcatgaaatc    1620
aaagaagaaa aagcgactcc ggcaatgcct gatatgggtg gcatgggcgg tatgggaggc    1680
atgggcggca tgatgtaagc ccgcttgctt tttagtataa tctgcttta aaatcccttc     1740 tctaaatccc ccctttcta aaatctcttt tttggggggg tgctttgata aaaccgctcg     1800
cttgtaaaaa catgcaacaa aaaatctctg ttaagctt                            1838
```

<210> SEQ ID NO 8
<211> LENGTH: 18
<212> TYPE: DNA
<213> ORGANISM: Artificial Sequence
<220> FEATURE:
<223> OTHER INFORMATION: primer oligonucleotide

<400> SEQUENCE: 8

```
gactcgagtc gacatcga                                                    18
```

<210> SEQ ID NO 9
<211> LENGTH: 12
<212> TYPE: PRT
<213> ORGANISM: Helicobacter pylori

<400> SEQUENCE: 9

Glu Phe Lys Asn Gly Lys Asn Lys Asp Phe Ser Lys
1               5                   10

<210> SEQ ID NO 10
<211> LENGTH: 5
<212> TYPE: PRT
<213> ORGANISM: Helicobacter pylori

<400> SEQUENCE: 10

Glu Pro Ile Tyr Ala
1               5

<210> SEQ ID NO 11
<211> LENGTH: 102
<212> TYPE: DNA
<213> ORGANISM: Helicobacter pylori

<400> SEQUENCE: 11

```
gggcgatcgg ttagccctga acccatttat gctacgattg atgatctccg gcggacctttt    60 cccttttgaaa ggcatgataa agttgatgat ctcagtaagg ta                      102
```

<210> SEQ ID NO 12
<211> LENGTH: 34
<212> TYPE: PRT

```
<213> ORGANISM: Helicobacter pylori

<400> SEQUENCE: 12

Gly Arg Ser Val Ser Pro Glu Pro Ile Tyr Ala Thr Ile Asp Asp Leu
1               5                  10                  15

Gly Gly Pro Phe Pro Leu Lys Arg His Asp Lys Val Asp Asp Leu Ser
            20                  25                  30

Lys Val

<210> SEQ ID NO 13
<211> LENGTH: 18
<212> TYPE: DNA
<213> ORGANISM: Helicobacter pylori

<400> SEQUENCE: 13
cctgaaccca tttatgct                                                18

<210> SEQ ID NO 14
<211> LENGTH: 6
<212> TYPE: PRT
<213> ORGANISM: Helicobacter pylori

<400> SEQUENCE: 14

Pro Glu Pro Ile Tyr Ala
1               5

<210> SEQ ID NO 15
<211> LENGTH: 9
<212> TYPE: DNA
<213> ORGANISM: Helicobacter pylori

<400> SEQUENCE: 15 gatgatctc                                                           9

<210> SEQ ID NO 16
<211> LENGTH: 3
<212> TYPE: PRT
<213> ORGANISM: Helicobacter pylori

<400> SEQUENCE: 16

Asp Asp Leu
1

<210> SEQ ID NO 17
<211> LENGTH: 15
<212> TYPE: PRT
<213> ORGANISM: Helicobacter pylori

<400> SEQUENCE: 17

Phe Pro Leu Lys Arg His Asp Lys Val Asp Asp Leu Ser Lys Val
1               5                  10                  15

<210> SEQ ID NO 18
<211> LENGTH: 45
<212> TYPE: DNA
<213> ORGANISM: Helicobacter pylori

<400> SEQUENCE: 18
tttccctttg aaaggcatga taaagttgat gatctcagta aggta                  45

<210> SEQ ID NO 19
<211> LENGTH: 36
<212> TYPE: DNA
```

<213> ORGANISM: Helicobacter pylori

<400> SEQUENCE: 19
gaattcaaaa atggcaaaaa taaggatttc agcaag                                    36

<210> SEQ ID NO 20
<211> LENGTH: 15
<212> TYPE: DNA
<213> ORGANISM: Helicobacter pylori

<400> SEQUENCE: 20
gaacccattt atgct                                                           15

<210> SEQ ID NO 21
<211> LENGTH: 15
<212> TYPE: DNA
<213> ORGANISM: Helicobacter pylori

<400> SEQUENCE: 21
gaacccattt acgct                                                           15

<210> SEQ ID NO 22
<211> LENGTH: 45
<212> TYPE: DNA
<213> ORGANISM: Helicobacter pylori

<400> SEQUENCE: 22
ttccctttga aaaggcatga taaagttgat gatctcagta aggta                          45

<210> SEQ ID NO 23
<211> LENGTH: 6
<212> TYPE: PRT
<213> ORGANISM: Helicobacter pylori

<400> SEQUENCE: 23

Asn Asn Asn Asn Asn Asn
1               5

<210> SEQ ID NO 24
<211> LENGTH: 18
<212> TYPE: DNA
<213> ORGANISM: Helicobacter pylori

<400> SEQUENCE: 24
aataacaata acaataat                                                        18

<210> SEQ ID NO 25
<211> LENGTH: 228
<212> TYPE: PRT
<213> ORGANISM: Helicobacter pylori

<400> SEQUENCE: 25

Lys Asn Gly Lys Asn Lys Asp Phe Ser Lys Val Thr Gln Ala Lys Ser
1               5                   10                  15

Asp Leu Glu Asn Ser Val Lys Asp Val Ile Ile Asn Gln Lys Val Thr
            20                  25                  30

Asp Lys Val Asp Asn Leu Asn Gln Ala Val Ser Val Ala Lys Ala Thr
        35                  40                  45

Gly Asp Phe Ser Arg Val Glu Gln Ala Leu Ala Asp Leu Lys Asn Phe
    50                  55                  60

Ser Lys Glu Gln Leu Ala Gln Gln Ala Gln Lys Asn Glu Ser Leu Asn
65                  70                  75                  80

Ala Arg Lys Lys Ser Glu Ile Tyr Gln Ser Val Lys Asn Gly Val Asn
                85                  90                  95

Gly Thr Leu Val Gly Asn Gly Leu Ser Gln Ala Glu Ala Thr Thr Leu
            100                 105                 110

Ser Lys Asn Phe Ser Asp Ile Lys Lys Glu Leu Asn Ala Lys Leu Gly
            115                 120                 125

Asn Phe Asn Asn Asn Asn Asn Gly Leu Lys Asn Glu Pro Ile Tyr
    130                 135                 140

Ala Lys Val Asn Lys Lys Ala Gly Gln Ala Ala Ser Leu Glu Glu
145                 150                 155                 160

Pro Ile Tyr Ala Gln Val Ala Lys Lys Val Asn Ala Lys Ile Asp Arg
                165                 170                 175

Leu Asn Gln Ile Ala Ser Gly Leu Gly Val Val Gly Gln Ala Ala Gly
            180                 185                 190

Phe Pro Leu Lys Arg His Asp Lys Val Asp Asp Leu Ser Lys Val Gly
            195                 200                 205

Leu Ser Arg Asn Gln Glu Leu Ala Gln Lys Ile Asp Asn Leu Asn Gln
    210                 215                 220

Ala Val Ser Glu
225

<210> SEQ ID NO 26
<211> LENGTH: 685
<212> TYPE: DNA
<213> ORGANISM: Helicobacter pylori

<400> SEQUENCE: 26
aaaaatggca aaataagga tttcagcaag gtaacgcaag caaaaagcga ccttgaaaat      60
tccgttaaag atgtgatcat caatcaaaag gtaacggata agttgataa tctcaatcaa    120 gcggtatcag tggctaaagc aacgggtgat tcagtaggg tagagcaagc gttagccgat    180
ctcaaaaatt tctcaaagga gcaattggcc caacaagctc aaaaaatga agtctcaat    240 gctagaaaaa atctgaaat atatcaatcc gttaagaatg gtgtgaatgg aaccctagtc    300
ggtaatgggt tatctcaagc agaagccaca actctttcta aaacttttc ggacatcaag    360 aaagagttga atgcaaaact tggaaatttc aataacaata caataatgg actcaaaaac    420 gaacccattt atgctaaagt taataaaaag aaagcagggc aagcagctag ccttgaagaa    480
cccatttacg ctcaagttgc taaaaaggta aatgcaaaaa ttgaccgact caatcaaata    540
gcaagtggtt tgggtgttgt agggcaagca gcgggcttcc ctttgaaaag gcatgataaa    600
gttgatgatc tcagtaaggt agggctttca aggaatcaag aattggctca gaaaattgac    660
aatctcaatc aagcggtatc agaag                                           685

<210> SEQ ID NO 27
<211> LENGTH: 699
<212> TYPE: DNA
<213> ORGANISM: Helicobacter pylori

<400> SEQUENCE: 27
gaattcaaaa atggcaaaaa taaggatttc agcaaggtaa cgcaagcaaa aagcgaccctt     60 gaaaattccg ttaaagatgt gatcatcaat caaaaggtaa cggataaagt tgataatctc    120
aatcaagcgg tatcagtggc taaagcaacg ggtgatttca gtagggtaga gcaagcgtta    180
gccgatctca aaaatttctc aaaggagcaa ttggcccaac aagctcaaaa aaatgaaagt    240

```
-continued ctcaatgcta gaaaaaatc tgaaatatat caatccgtta agaatggtgt gaatggaacc      300
ctagtcggta atgggttatc tcaagcagaa gccacaactc tttctaaaaa cttttcggac      360
atcaagaaag agttgaatgc aaaacttgga aatttcaata acaataacaa taatggactc      420
aaaaacgaac ccatttatgc taaagttaat aaaaagaaag cagggcaagc agctagcctt      480
gaagaaccca tttacgctca agttgctaaa aaggtaaatg caaaaattga ccgactcaat      540
caaatagcaa gtggtttggg tgttgtaggg caagcagcgg gcttcccttt gaaaaggcat      600
gataaagttg atgatctcag taaggtaggg ctttcaagga atcaagaatt ggctcagaaa      660
attgacaatc tcaatcaagc ggtatcagaa gccgaattc                            699

<210> SEQ ID NO 28
<211> LENGTH: 15
<212> TYPE: PRT
<213> ORGANISM: Helicobacter pylori

<400> SEQUENCE: 28

Phe Pro Leu Lys Arg His Asp Lys Val Asp Asp Leu Ser Lys Val
1               5                   10                  15

<210> SEQ ID NO 29
<211> LENGTH: 6
<212> TYPE: PRT
<213> ORGANISM: Helicobacter pylori

<400> SEQUENCE: 29

Asn Glu Pro Ile Tyr Ala
1               5

<210> SEQ ID NO 30
<211> LENGTH: 6
<212> TYPE: PRT
<213> ORGANISM: Helicobacter pylori

<400> SEQUENCE: 30

Glu Glu Pro Ile Tyr Ala
1               5
```

HELICOBACTER PYLORI PROTEINS USEFUL FOR VACCINES AND DIAGNOSTICS

This application is a divisional of U.S. application Ser. No. 08/471,491, filed Jun. 6, 1995, now U.S. Pat. No. 6,090,611, which is a divisional of U.S. application Ser. No. 08/256,848, filed Oct. 21, 1994, now abandoned, which is a U.S. national phase application of PCT/EP93/00472, filed Mar. 2, 1993 and PCT/EP93/00158, filed Jan. 25, 1993, which two PCT applications claimed priority benefit of Italian application Serial No. FI 92 A 000052, filed Mar. 2, 1992, the entire contents of each application is incorporated by reference herein.

BACKGROUND OF THE INVENTION

1. Field of the Disclosure

The present invention relates generally to certain *Helicobacter pylori* proteins, to the genes which express these proteins, and to the use of these proteins for diagnostic and vaccine applications.

2. Brief Description of Related Art

*Helicobacter pylori* is a curved, microaerophilic, gram negative bacterium that has been isolated for the first time in 1982 from stomach biopsies of patients with chronic gastritis, Warren et al., Lancet i:1273–75 (1983). Originally named *Campylobacter pylori*, it has been recognized to be part of a separate genus named *Helicobacter*, Goodwin et al., Int. J. Syst. Bacteriol. 39:397–405 (1989). The bacterium colonizes the human gastric mucosa, and infection can persist for decades. During the last few years, the presence of the bacterium has been associated with chronic gastritis type B, a condition that may remain asymptomatic in most infected persons but increases considerably the risk of peptic ulcer and gastric adenocarcinoma. The most recent studies strongly suggest that *H. pylori* infection may be either a cause or a cofactor of type B gastritis, peptic ulcers, and gastric tumors, see e.g., Blaser, Gastroenterology 93:371–83 (1987); Dooley et al., New Engl. J. Med. 321:1562–66 (1989); Parsonnet et al., New Engl. J. Med. 325:1127–31 (1991). *H. pylori* is believed to be transmitted by the oral route, Thomas et al., Lancet i:340, 1194 (1992), and the risk of infection increases with age, Graham et al., Gastroenterology 100:1495–1501 (1991), and is facilitated by crowding, Drumm et al., New Engl. J. Med. 4322:359–63 (1990); Blaser, Clin. Infect. Dis. 15:386–93 (1992). In developed countries, the presence of antibodies against *H. pylori* antigens increases from less than 20% to over 50% in people 30 and 60 years old respectively, Jones et al., Med. Microbio. 22:57–62 (1986); Morris et al., N. Z. Med. J. 99:657–59 (1986), while in developing countries over 80% of the population are already infected by the age of 20, Graham et al., Digestive Diseases and Sciences 36:1084–88 (1991).

The nature and the role of the virulence factors of *H. pylori* are still poorly understood. The factors that have been identified so far include the flagella that are probably necessary to move across the mucus layer, see e.g., Leying et al., Mol. Microbiol. 6:2863–74 (1992); the urease that is necessary to neutralize the acidic environment of the stomach and to allow initial colonization, see e.g., Cussac et al., J. Bacteriol. 174:2466–73 (1992); Perez-Perez et al., J. Infect. Immun. 60:3658–3663 (1992); Austin et al., J. Bacteriol. 174:7470–73 (1992); PCT Publ. No. WO 90/04030; and a high molecular weight cytotoxic protein formed by monomers allegedly having a molecular weight of 87 kDa that causes formation of vacuoles in eukaryotic epithelial cells and is produced by *H. pylori* strains associated with disease, see e.g., Cover et al., J. Bio. Chem. 267:10570–75 (1992) (referencing a "vacuolating toxin" with a specified 23 amino acid N-terminal sequence); Cover et al., J. Clin. Invest. 90:913–18 (1992); Leunk, Rev. Infect. Dis. 13:5686–89 (1991). Additionally, the following is also known.

*H. pylori* culture supernatants have been shown by different authors to contain an antigen with a molecular weight of 120, 128, or 130 kDa, Apel et al., Aentralblat fur Bakteriol. Microb. und Hygiene 268:271–76 (1988); Crabtree et al., J. Clin. Pathol 45:733–34 (1992); Cover et al., Infect. Immun. 58:603–10 (1990); Figura et al., *H. pylori*, gastritis and peptic ulcer (eds. Malfrtheiner et al.), Springer Verlag, Berlin (1990). Whether the difference in size of the antigen described was due to interlaboratory differences in estimating the molecular weight of the same protein, to the size variability of the same antigen, or to actual different proteins was not clear. No nucleotide or amino acid sequence information was given about the protein. This protein is very immunogenic in infected humans because specific antibodies are detected in sera of virtually all patients infected with *H. pylori*, Gerstenecker et al., Eur. J. Clin. Microbiol. 11:595–601 (1992).

*H. pylori* heat shock proteins (hsp) have been described, Evans et al., Infect. Immun. 60:2125–27 (1992) (44 amino acid N-terminal sequence and a molecular weight of about 62 kDa); Dunn et al., Infect. Immun. 60:1946–51 (1992) (33 amino acids found in the N-terminal sequence and a molecular weight of about 54 kDa); Austin et al., J. Bacteriol. 174:7470–73 (1992) (37 amino acids found in the N-terminal sequence and a molecular weight of about 60 kDa). Austin et al. suggest that these are, in fact, the same protein with identical amino acid sequences at their N-terminus.

For examples of diagnostic tests based on *H. pylori* lysates or semipurified antigens, see Evans et al., Gastroenterology 96:1004–08 (1989); U.S. Pat. No. 4,882,271; PCT Publ. No. WO 89/08843 (all relating to compositions and assays containing the same having high molecular weight antigens (300–700 kDa) from the outer membrane surface with urease activity); EPO Publ. No. 329 570 (relating to antigenic compositions for detecting *H. pylori* antibodies having fragments of at least one fragment from the group 63, 57, 45, and 31 kDa).

The percentage of people infected by *H. pylori*, either in a symptomatic or an asymptomatic form, is very high in both developing and developed countries, and the cost of hospitalization and therapy makes desirable the development of both *H. pylori* vaccines and further diagnostic tests for this disease.

SUMMARY OF THE INVENTION

The present invention describes nucleotide and amino acid sequences for three major *H. pylori* proteins. Specifically, these are the cytotoxin, the "Cytotoxin Associated Immunodominant" (CAI) antigen, and the heat shock protein. None of the complete amino acid sequences for these proteins has been known, nor have their genes been identified. The present invention pertains to not only these purified proteins and their genes, but also recombinant materials associated therewith, such as vectors and host cells. The present invention provides cytotoxin polypeptides that exhibit substantially no toxicity, or substantially reduced toxicity. The present invention also provides CAI and heat shock polypeptides that exhibit no functional contribution to toxicity, or a substantially reduced functional contribution to toxicity. The understanding at the molecular level of the nature and the role of these proteins and the availability of recombinant production has important implications for the development of new diagnostics for *H. pylori* and for the design of vaccines that may prevent *H. pylori* infection and treat disease.

As such, these proteins can be used in both vaccine and diagnostic applications. The present invention includes methods for treating and diagnosing those diseases associated with *H. pylori*. As *H. pylori* has been associated with type B gastritis, peptic ulcers, and gastric adenocarcinoma, it is hoped that the present invention will assist in early detection and alleviation of these disease states. Currently, diagnosis relies mostly on endoscopy and histological staining of biopsies; existing immunoassays are based on *H. pylori* lysates or semi-purified antigens. Given the heterogeneity found in such assays, correlation with disease state is not yet well established. Thus, the potential for recombinant antigen-based immunoassays, as well as nucleic acid assays for disease detection, is great. At present, there is no commercial vaccine for *H. pylori* infection or treatment. A recombinant vaccine is thus an object of the present invention.

BRIEF DESCRIPTION OF THE DRAWINGS

FIGS. 1A 1B and 1C (SEQ. ID. NO.2) is the nucleotide sequence for the cytotoxin (CT) protein.

FIG. 2 (SEQ. ID. NO.3) is the amino acid sequence for the cytotoxin (CT) protein.

FIGS. 4A through 4F (SEQ ID NO:4 and SEQ ID NO:5) the nucleotide and amino acid sequences of the CAI antigen. The numbers along the left hand margins of FIGS. 4A, 4C and 4E designate the amino acid positions. Shown boxed in FIGS. 4C–D are two repeats of the peptide EFKNGKNKDFSK (SEQ ID NO:9), which are encoded by the nucleic acid sequence of SEQ ID NO:19. Also shown boxed in FIGS. 4C–D are two repeats of the peptide EPIYA (SEQ ID NO:10), the first of which is encoded by the nucleic acid sequence of SEQ ID NO:20, the second of which is encoded by the nucleic acid sequence of SEQ ID NO:21. Also shown boxed in FIGS. 4C–D is the peptide FPLKRHDKVDDLSKV (SEQ ID NO:28), which is encoded by the nucleic acid sequence of SEQ ID NO:22.

FIG. 5 is the nucleotide and amino acid sequences of the heat shock protein (hsp).

DETAILED DESCRIPTION OF THE INVENTION

A. General Methodology

Figure 3:
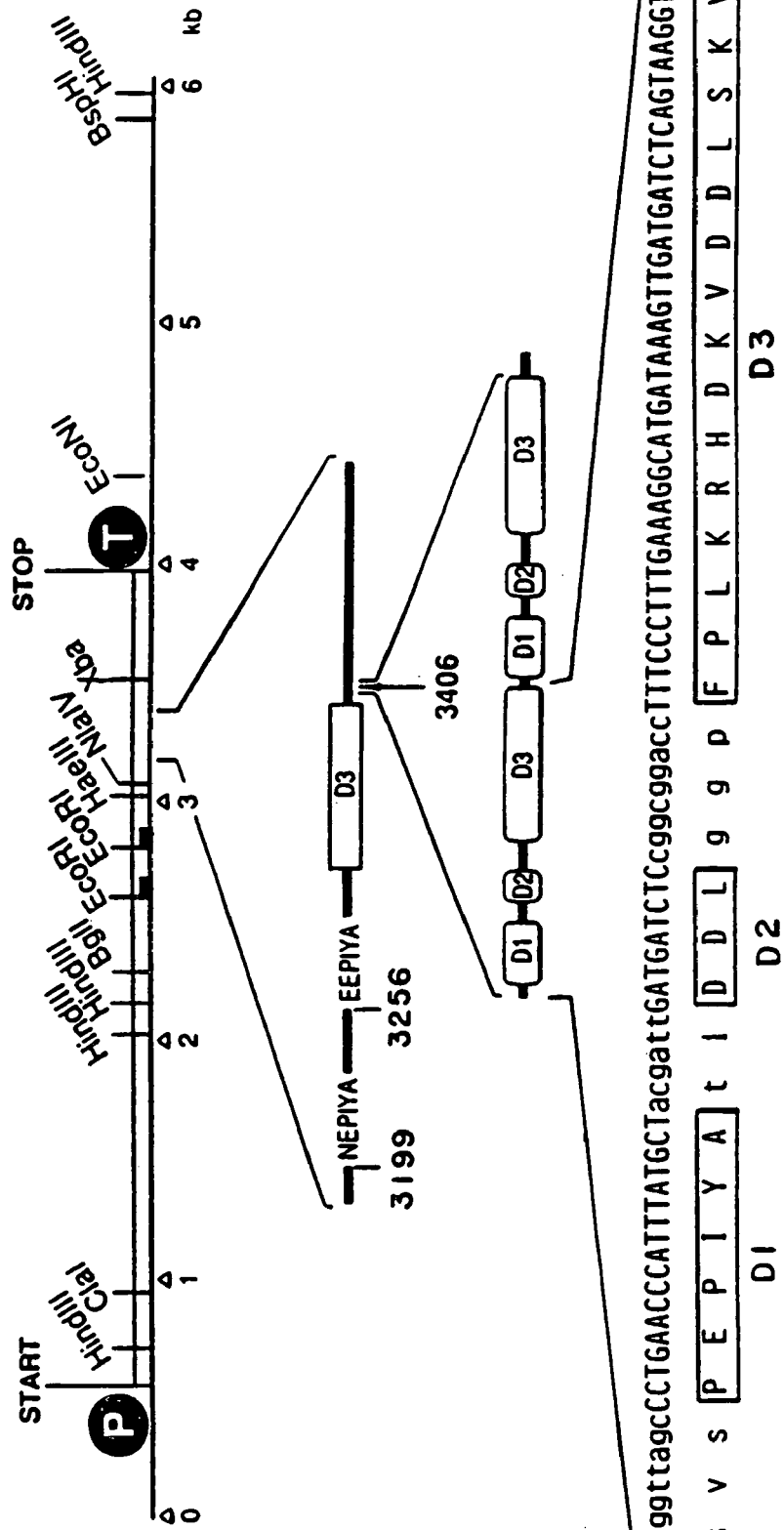
FIG. 3 is a map of the cai gene for the CAI protein and summary of the clones used to identify and sequence this gene. In the middle of FIG. 3, upstream of the D3 box, two short peptide sequences are shown: "NEPIYA" (SEQ ID NO:29) and "EEPIYA" (SEQ ID NO:30). At the bottom of the FIG. 3, the nucleotide (SEQ ID NO:11) and deduced amino acid sequence (SEQ ID NO:12) of the cloned segment is shown with peptides D1 (SEQ ID NO:14), D2 (SEQ ID NO:16) and D3 (SEQ ID NO:17) shown boxed.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Standard abbreviations for nucleotides and amino acids are used in this specification. All publications, patents, and patent applications cited herein are incorporated by reference.

B. Definitions

"Cytotoxin" or "toxin" of *H. pylori* refers to the protein, and fragments thereof, whose nucleotide sequence and amino acid sequences are shown in FIGS. 1 and 2, respectively, and their derivatives, and whose molecular weight is about 140 kDa. This protein serves as a precursor to a protein having an approximate weight of 100 kDa and having cytoxic activity. The cytotoxin causes vacuolation and death of a number of eukaryotic cell types and has been purified from *H. pylori* culture supernatants. Additionally, the cytotoxin is proteinaceous and has an apparent molecular mass determined by gel filtration of approximately 950–972 kDa. Denaturing gel electrophoresis of purified material previously revealed that the principal component of the 950–972 kDa molecule was allegedly a polypeptide of apparent molecular mass of 87 kDa, Cover et al., J. Biol. Chem. 267:10570–75 1992). It is suggested herein, however, that the previously described 87 kDa results from either the further processing of the 100 kDa protein or from proteolytic degradation of a larger protein during purification.

The "Cytotoxin Associated Immunodominant" (CAI) antigen refers to that protein, and fragments thereof, whose amino acid sequence is described in FIG. 4 and derivatives thereof. The CAI antigen is about 130 kDa as determined by SDS/polyacrylamide gel electrophoresis and comprises the following amino acid sequence (SEQ ID NO: 25):

1                    LysAsnGlyLysAsnLysAspPhe-
    SerLysValThrGlnAlaLysSerAspLeuGluAsn 20
21                    SerValLysAspValIleIleAs-
    nGlnLysValThrAspLysValAspAsnLeuAsnGln 40
41                    AlaValSerValAlaLysAlaThrGl-
    yAspPheSerArgValGluGlnAlaLeuAlaAsp 60
61                    LeuLysAsnPheSerLysGluGln-
    LeuAlaGlnGlnAlaGlnLysAsnGluSerLeuAsn 80
81                    AlaArgLysLysSerGluIleTyrGln-
    SerValLysAsnGlyValAsnGlyThrLeuVal 100
101                    GlyAsnGlyLeuSerGlnAlaGlu-
    AlaThrThrLeuSerLysAsnPheSerAspIleLys 120
121                    LysGluLeuAsnAlaLysLeuGlyAsn-
    PheAsnAsnAsnAsnAsnAsnGlyLeuLysAsn 140

141 GluProIleTyrAlaLysValAsnLysLysLysAlaGlyGlnAlaAlaSerLeuGluGlu 160
161 ProIleTyrAlaGlnValAlaLysLysValAsnAlaLysIleAspArgLeuAsnGlnIle 180
181 AlaSerGlyLeuGlyValValGlyGlnAlaAlaGlyPheProLeuLysArgHisAspLys 200
201 ValAspAspLeuSerLysValGlyLeuSerArgAsnGlnGluLeuAlaGlnLysIleAsp 220
221 AsnLeuAsnGlnAlaValSerGlu 228

SEQ ID NO: 25 is the protein encoded by the nucleotides 7 to 690 of the sequenced DNA having the following nucleotide sequence of SEQ ID NO: 27, wherein the uppercase letters represent the cloned nucleotide sequence of SEQ ID NO: 26 and the lower case letters represent the EcoRI site:

1 gaattcAAAAATGGCAAAAATAAGGATTTCAGCAAGGTAACGCAAGCAAAAAGCGACCTT 60
61 GAAAATTCCGTTAAAGATGTGATCATCAATCAAAAGGTAACGGATAAAGTTGATAATCTC 120
121 AATCAAGCGGTATCAGTGGCTAAAGCAACGGGTGATTTCAGTAGGGTAGAGCAAGCGTTA 180
181 GCCGATCTCAAAAATTTCTCAAAGGAGCAATTGGCCCAACAAGCTCAAAAAAATGAAAGT 240
241 CTCAATGCTAGAAAAAAATCTGAAATATATCAATCCGTTAAGAATGGTGTGAATGGAACC 300
301 CTAGTCGGTAATGGGTTATCTCAAGCAGAAGCCACAACTCTTTCTAAAAACTTTTCGGAC 360
361 ATCAAGAAAGAGTTGAATGCAAAACTTGGAAATTTCAATAACAATAACAATAATGGACTC 240
421 AAAAACGAACCCATTTATGCTAAAGTTAATAAAAAGAAAGCAGGGCAAGCAGCTAGCCTT 480
481 GAAGAACCCATTTACGCTCAAGTTGCTAAAAAGGTAAATGCAAAAATTGACCGACTCAAT 540
541 CAAATAGCAAGTGGTTTGGGTGTTGTAGGGCAAGCAGCGGGCTTCCCTTTGAAAAGGCAT 600
601 GATAAAGTTGATGATCTCAGTAAGGTAGGGCTTTCAAGGAATCAAGAATTGGCTCAGAAA 660
661 ATTGACAATCTCAATCAAGCGGTATCAGAAGccgaattc 669

"Heat shock protein" (hsp) refers to the *H. pylori* protein, and fragments thereof, whose amino acid sequence is given in FIG. 5 and derivatives thereof, and whose molecular weight is in the range of 54–62 kDa, preferably about 58–60 kDa. This hsp belongs to the group of Gram negative bacteria heat shock-proteins, hsp60. In general, hsp are among the most conserved proteins in all living organisms, either prokaryotic and eukaroytic, animals and plants, and the conservation is spread along the whole sequence. This high conservation suggests a participation of the whole sequence at the functional structure of the protein that can be hardly modified without impairing its activity.

Examples of proteins that can be used in the present invention include polypeptides with minor amino acid variations from the natural amino acid sequence of the protein; in particular, conservative amino acid replacements are contemplated. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an aspartate with a glutamate, a threonine with a serine, or a similar conservative replacement of an amino acid with a structurally related amino acid will not have a major effect on the biological activity. Polypeptide molecules having substantially the same amino acid sequence as the protein but possessing minor amino acid substitutions that do not substantially affect the functional aspects are within the definition of the protein.

A significant advantage of producing the protein by recombinant DNA techniques rather than by isolating a purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant non-human host is the recombinant protein at issue. Potential viral agents from natural sources and viral components pathogenic to humans are also avoided.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, this term also encompasses the situation wherein the *H. pylori* bacterium genome is genetically modified (e.g., through mutagenesis) to produce one or more altered polypeptides.

The term "polynucleotide" as used herein refers to a polymeric form of a nucleotide of any length, preferably deoxyribonucleotides, and is used interchangeably herein with the terms "oligonucleotide" and "oligomer." The term refers only to the primary structure of the molecule. Thus, this term includes double- and single-stranded DNA, as well as antisense polynucleotides. It also includes known types of modifications, for example, the presence of labels which are known in the art, methylation, end "caps," substitution of one or more of the naturally occurring nucleotides with an analog, internucleotide modifications such as, for example, replacement with certain types of uncharged linkages (e.g., methyl phosphonates, phosphotriesters, phosphoamidates, carbamates, etc.) or charged linkages (e.g., phosphorothioates, phosphorodithioates, etc.), introduction of pendant moieties, such as, for example, proteins (including nucleases, toxins, antibodies, signal peptides, poly-L-lysine, etc.), intercalators (e.g., acridine, psoralen, etc.), chelators (e.g., metals, radioactive species, boron, oxidative moieties, etc.), alkylators (e.g., alpha anomeric nucleic acids, etc.).

By "genomic" is meant a collection or library of DNA molecules which are derived from restriction fragments that have been cloned in vectors. This may include all or part of the genetic material of an organism.

By "cDNA" is meant a complimentary mRNA sequence that hybridizes to a complimentary strand of mRNA.

As used herein, the term "oligomer" refers to both primers and probes and is used interchangeably herein with the term "polynucleotide." The term oligomer does not connote the size of the molecule. However, typically oligomers are no greater than 1000 nucleotides, more typically are no greater than 500 nucleotides, even more typically are no greater than 250 nucleotides; they may be no greater than 100 nucleotides, and may be no greater than 75 nucleotides, and also may be no greater than 50 nucleotides in length.

The term "primer" as used herein refers to an oligomer which is capable of acting as a point of initiation of synthesis of a polynucleotide strand when used under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer will be extended by the polymerizing agent to form a copy of the analyte strand. The primer may be single-stranded or alternatively may be partially or fully double-stranded.

The terms "analyte polynucleotide" and "analyte strand" refer to a single- or double-stranded nucleic acid molecule which is suspected of containing a target sequence, and which may be present in a biological sample.

As used herein, the term "probe" refers to a structure comprised of a polynucleotide which forms a hybrid structure with a target sequence, due to complementarily of at least one sequence in the probe with a sequence in the target region. The polynucleotide regions of probes may be composed of DNA, and/or RNA, and/or synthetic nucleotide analogs. Included within probes are "capture probes" and "label probes".

As used herein, the term "target region" refers to a region of the nucleic acid which is to be amplified and/or detected. The term "target sequence" refers to a sequence with which a probe or primer will form a stable hybrid under desired conditions.

The term "capture probe" as used herein refers to a polynucleotide probe comprised of a single-stranded polynucleotide coupled to a binding partner. The single-stranded polynucleotide is comprised of a targeting polynucleotide sequence, which is complementary to a target sequence in a target region to be detected in the analyte polynucleotide. This complementary region is of sufficient length and complementarily to the target sequence to afford a duplex of stability which is sufficient to immobilize the analyte polynucleotide to a solid surface (via the binding partners). The binding partner is specific for a second binding partner; the second binding partner can be bound to the surface of a solid support, or may be linked indirectly via other structures or binding partners to a solid support.

The term "targeting polynucleotide sequence" as used herein refers to a polynucleotide sequence which is comprised of nucleotides which are complementary to a target nucleotide sequence; the sequence is of sufficient length and complementarily with the target sequence to form a duplex which has sufficient stability for the purpose intended.

The term "binding partner" as used herein refers to a molecule capable of binding a ligand molecule with high specificity, as for example an antigen and an antibody specific therefor. In general, the specific binding partners must bind with sufficient affinity to immobilize the analyte copy/complementary strand duplex (in the case of capture probes) under the isolation conditions. Specific binding partners are known in the art, and include, for example, biotin and avidin or streptavidin, IgG and protein A, the numerous known receptor-ligand couples, and complementary polynucleotide strands. In the case of complementary polynucleotide binding partners, the partners are normally at least about 15 bases in length, and may be at least 40 bases in length; in addition, they have a content of Gs and Cs of at least about 40% and as much as about 60%. The polynucleotides may be composed of DNA, RNA, or synthetic nucleotide analogs.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

The term "support" refers to any solid or semi-solid surface to which a desired binding partner may be anchored. Suitable supports include glass, plastic, metal, polymer gels, and the like, and may take the form of beads, wells, dipsticks, membranes, and the like.

The term "label" as used herein refers to any atom or moiety which can be used to provide a detectable (preferably quantifiable) signal, and which can be attached to a polynucleotide or polypeptide.

As used herein, the term "label probe" refers to a polynucleotide probe which is comprised of a targeting polynucleotide sequence which is complementary to a target sequence to be detected in the analyte polynucleotide. This complementary region is of sufficient length and complementarily to the target sequence to afford a duplex comprised of the "label probe" and the "target sequence" to be detected by the label. The label probe is coupled to a label either directly, or indirectly via a set of ligand molecules with high specificity for each other, including multimers.

The term "multimer," as used herein, refers to linear or branched polymers of the same repeating single-stranded polynucleotide unit or different single-stranded polynucleotide units. At least one of the units has a sequence, length, and composition that permits it to hybridize specifically to a first single-stranded nucleotide sequence of interest, typically an analyte or a polynucleotide probe (e.g., a label probe) bound to an analyte. In order to achieve such specificity and stability, this unit will normally be at least about 15 nucleotides in length, typically no more than about 50 nucleotides in length, and preferably about 30 nucleotides in length; moreover, the content of Gs and Cs will normally be at least about 40%, and at most about 60%. In addition to such unit(s), the multimer includes a multiplicity of units that are capable of hybridizing specifically and stably to a second single-stranded nucleotide of interest, typically a labeled polynucleotide or another multimer. These units are generally about the same size and composition as the multimers discussed above. When a multimer is designed to be hybridized to another multimer, the first and second oligonucleotide units are heterogeneous (different), and do not hybridize with each other under the conditions of the selected assay. Thus multimers may be label probes, or may be ligands which couple the label to the probe.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

"PCR" refers to the technique of polymerase chain reaction as described in Saiki, et al., Nature 324:163 (1986); and Scharf et al., Science (1986) 233:1076–1078; and U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

"Immunogenic" refers to the ability of a polypeptide to cause a humoral and/or cellular immune response, whether alone or when linked to a carrier, in the presence or absence of an adjuvant. "Neutralization" refers to an immune response that blocks the infectivity, either partially or fully, of an infectious agent.

"Epitope" refers to an antigenic determinant of a peptide, polypeptide, or protein; an epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Antibodies that recognize the same epitope can be identified in a simple immunoassay showing the ability of one antibody to block the binding of another antibody to a target antigen.

"Treatment," as used herein, refers to prophylaxis and/or therapy (i.e., the modulation of any disease symptoms). An "individual" indicates an animal that is susceptible to infection by *H. pylori* and includes, but is not limited to, primates, including humans. A "vaccine" is an immunogenic, or otherwise capable of eliciting protection against *H. pylori*, whether partial or complete, composition useful for treatment of an individual.

The *H. pylori* proteins may be used for producing antibodies, either monoclonal or polyclonal, specific to the proteins. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85%, by weight, more preferably still at least 95% by weight, and most preferably at least 98% by weight, of biological macromolecules of the same type present (but water, buffers, and other small molecules, especially molecules having a molecular weight of less than 1000, can be present).

C. Nucleic Acid Assays

Using as a basis the genome of *H. pylori*, poly-nucleotide probes of approximately 8 nucleotides or more can be prepared which hybridize with the positive strand(s) of the RNA or its complement, as well as to cDNAs. These polynucleotides serve as probes for the detection, isolation and/or labeling of polynucleotides which contain nucleotide sequences, and/or as primers for the transcription and/or replication of the targeted sequences. Each probe contains a targeting polynucleotide sequence, which is comprised of nucleotides which are complementary to a target nucleotide sequence; the sequence is of sufficient length and complementarily with the sequence to form a duplex which has sufficient stability for the purpose intended. For example, if the purpose is the isolation, via immobilization, of an analyte containing a target sequence, the probes will contain a polynucleotide region which is of sufficient length and complementarily to the targeted sequence to afford sufficient duplex stability to immobilize the analyte on a solid surface under the isolation conditions. For example, also, if the polynucleotide probes are to serve as primers for the transcription and/or replication of target sequences, the probes will contain a polynucleotide region of sufficient length and complementarily to the targeted sequence to allow for replication. For example, also, if the polynucleotide probes are to be used as label probes, or are to bind to multimers, the targeting polynucleotide region would be of sufficient length and complementarily to form stable hybrid duplex structures with the label probes and/or multimers to allow detection of the duplex. The probes may contain a minimum of about 4 contiguous nucleotides which are complementary to the targeted sequence; usually the oligomers will contain a minimum of about 8 continuous nucleotides which are complementary to the targeted sequence, and preferably will contain a minimum of about 14 contiguous nucleotides which are complementary to the targeted sequence.

The probes, however, need not consist only of the sequence which is complementary to the targeted sequence. They may contain additional nucleotide sequences or other moieties. For example, if the probes are to be used as primers for the amplification of sequences via PCR, they may contain sequences which, when in duplex, form restriction enzyme sites which facilitate the cloning of the amplified sequences. For example, also, if the probes are to be used as "capture probes" in hybridization assays, they will be coupled to a "binding partner" as defined above. Preparation of the probes is by means known in the art, including, for example, by methods which include excision, transcription or chemical synthesis.

D. Expression Systems

Once the appropriate *H. pylori* coding sequence is isolated, it can be expressed in a variety of different expression systems; for example those used with mammalian cells, baculoviruses, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation, Sambrook et al., *Molecular Cloning: A Laboratory Manual*, 2nd ed (1989).

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter, Maniatis et al., Science 236:1237 (1989); Alberts et al. *Molecular Biology of the Cell*, 2nd ed (1989). Enhancer elements derived from viruses may be particularly useful, because they usually have a broader host range. Examples include the SV40 early gene enhancer, Dijkema et al (1985) EMBO J. 4:761, and the enhancer/promoters derived from the long terminal repeat (LTR) of the Rous Sarcoma Virus, Gorman et al. (1982) Proc. Natl. Acad. Sci. 79:6777, and from human cytomegalovirus, Boshart et al. (1985) Cell 41:5221. Additionally, some enhancers are regulatable and become active only in the presence of an inducer, such as a hormone or metal ion, Sassone-Corsi et al. (1986) Trends Genet. 2:215; Maniatis et al. (1987) Science 236:1237.

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus tripartite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation, Birnstiel et al. (1985) Cell 41:349; Proudfoot and Whitelaw (1988) "Termination and 3' end processing of eukaryotic RNA. In Transcription and splicing (ed. B. D. Hames and D. M. Glover); Proudfoot (1989) Trends Biochem. Sci. 14:105. These sequences direct the transcription of an mRNA which can be translated into the polypeptide encoded by the DNA. Examples of transcription terminator/polyadenylation signals include those derived from SV40, Sambrook et al (1989), *Molecular Cloning: A Laboratory Manual*.

Some genes may be expressed more efficiently when introns (also called intervening sequences) are present. Several cDNAs, however, have been efficiently expressed from vectors that lack splicing signals (also called splice donor and acceptor sites), see e.g., Gething and Sambrook (1981) Nature 293:620. Introns are intervening noncoding sequences within a coding sequence that contain splice donor and acceptor sites. They are removed by a process called "splicing," following polyadenylation of the primary transcript, Nevins (1983) Annu. Rev. Biochem. 52:441; Green (1986) Annu. Rev. Genet. 20:671; Padgett et al. (1986) Annu. Rev. Biochem. 55:1119; Krainer and Maniatis (1988) "RNA splicing," In Transcription and splicing (ed. B. D. Hames and D. M. Glover);

Usually, the above-described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40, Gluzman (1981) Cell 23:175, or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2, Kaufman et al. (1989) Mol. Cell. Biol. 9:946, and PHEBO, Shimizu et al. (1986) Mol. Cell. Biol. 6:1074.

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, Texas Agricultural Experiment Station Bulletin No. 1555 (1987) (hereinafter "Summers and Smith").

Prior to inserting the DNA sequence encoding the protein into the baculovirus genome, the above-described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, Virology (1989) 17:31.

The plasmid usually also contains the polyhedron polyadenylation signal (Miller et al. (1988) Ann. Rev. Microbiol., 42:177) and a procaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfier); EPO Publ. Nos. 127 839 and 155 476; and the gene encoding the p10 protein, Vlak et al., (1988), J. Gen. Virol. 69:765.

DNA encoding suitable signal sequences can be derived from genes for secreted insect or baculovirus proteins, such as the baculovirus polyhedrin gene (Carbonell et al. (1988) Gene, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), Nature 315:592; human gastrin-releasing peptide, Lebacq-Verheyden et al., (1988), Molec. Cell. Biol. 8:3129; human IL-2, Smith et al., (1985) Proc. Nat'l Acad. Sci. USA, 82:8404; mouse IL-3, (Miyajima et al., (1987) Gene 58:273; and human glucocerebrosidase, Martin et al. (1988) DNA 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5 kb section of the baculovirus genome. Methods for introducing heterologous DNA into the desired site in the baculovirus virus are known in the art. (See Summers and Smith; Ju et al. (1987); Smith et al., Mol. Cell. Biol. (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), Bioessays 4:91.

The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (PCT Pub. No. WO 89/046699; Carbonell et al., (1985) J. Virol. 56:153; Wright (1986) Nature 321:718; Smith et al., (1983) Mol. Cell. Biol. 3:2156; and see generally, Fraser, et al. (1989) In Vitro Cell. Dev. Biol. 25:225).

Cells and cell culture media are commercially available for both direct and fusion expression of heterologous polypeptides in a baculovirus/expression system; cell culture technology is generally known to those skilled in the art. See, e.g., Summers and Smith.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli*, Raibaud et al. (1984) Annu. Rev. Genet. 18:173. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac), Chang et al. (1977) Nature 198:1056, and maltose. Additional examples include promoter sequences derived from biosynthetic enzymes such as tryptophan (trp), Goeddel et al. (1980) Nuc. Acids Res. 8:4057; Yelverton et al. (1981) Nucl. Acids Res. 9:731; U.S. Pat. No. 4,738,921; EPO Publ. Nos. 036 776 and 121 775. The glaotamase (bla) promoter system, Weissmann (1981) "The cloning of interferon and other mistakes." In *Interferon* 3 (ed. I. Gresser), bacteriophage lambda PL, Shimatake et al. (1981) Nature 292:128, and T5, U.S. Pat. No. 4,689,406, promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter, U.S. Pat. No. 4,551,433. For example, the tac promoter is a hybrid trp-lac promoter comprised of both trp promoter and lac operon sequences that is regulated by the lac repressor, Amann et al. (1983) Gene 25:167; de Boer et al. (1983) Proc. Natl. Acad. Sci. 80:21. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system, Studier et al. (1986) J. Mol. Biol. 189:113; Tabor et al. (1985) Proc Natl. Acad. Sci. 82:1074. In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon, Shine et al. (1975) Nature 254:34. The SD sequence is thought to promote binding of mRNA to the ribosome by the pairing of bases between the SD sequence and the 3' and of *E. coli* 16S rRNA, Steitz et al. (1979) "Genetic signals and nucleotide sequences in messenger RNA." In *Biological Regulation and Development: Gene Expression* (ed. R. F. Goldberger). To express eukaryotic genes and prokaryotic genes with weak ribosome-binding site, Sambrook et al. (1989), *Molecular Cloning: A Laboratory Manual*.

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene, Nagai et al. (1984) Nature 309:810. Fusion proteins can also be made with sequences from the lacZ, Jia et al. (1987) Gene 60:197, trpE, Allen et al. (1987) J. Biotechnol. 5:93; Makoff et al. (1989) J. Gen. Microbiol. 135:11, and EPO Publ. No. 324 647, genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated. Miller et al. (1989) Bio/Technology 7:698.

Alternatively, foreign proteins can also be secreted from the cell by creating chimeric DNA molecules that encode a fusion protein comprised of a signal peptide sequence fragment that provides for secretion of the foreign protein in bacteria, U.S. Pat. No. 4,336,336. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA). Masui et al. (1983), in: *Experimental Manipulation of Gene Expression*; Ghrayeb et al. (1984) EMBO J. 3:2437 and the *E. coli* alkaline phosphatase signal sequence (phoA), Oka et al. (1985) Proc. Natl. Acad. Sci. 82:7212. As an additional example, the signal sequence of the alpha-amylase gene from various *Bacillus* strains can be used to secrete heterologous proteins from *B. subtilis*. Palva et al. (1982) Proc. Natl. Acad. Sci. USA 79:5582; EPO Publ. No. 244 042.

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above-described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline. Davies et al. (1978) Annu. Rev. Microbiol. 32:469. Selectable markers may also include biosynthetic genes, such as those in the histidine, tryptophan, and leucine biosynthetic pathways.

Alternatively, some of the above-described components can be put together in transformation vectors. Transformation vectors are usually comprised of a selectable marker that is either maintained in a replicon or developed into an integrating vector.

Expression and transformation vectors, either extra-chromosomal replicons or integrating vectors, have been developed for transformation into many bacteria. For example, expression vectors have been developed for, inter alia, the following bacteria: *Bacillus subtilis*, Palv et al. (1982) Proc. Natl. Acad. Sci. USA 79:5582; EPO Publ. Nos. 036 259 and 063 953; PCT Publ. No. WO 84/04541; *E. coli*, Shimatake et al. (1981) Nature 292:128; Amann et al. (1985) Gene 40:183; Studier et al. (1986) J. Mol. Biol. 189:113; EPO Publ. Nos. 036 776, 136 829 and 136 907; *Streptococcus cremoris*, Powell et al. (1988) Appl. Environ. Microbiol. 54:655; *Streptococcus lividans*, Powell et al. (1988) Appl. Environ. Microbiol. 54:655; and *Streptomyces lividans*, U.S. Pat. No. 4,745,056.

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See, e.g., Masson et al. (1989) FEMS Microbiol. Lett. 60:273; Palva et al. (1982) Proc. Natl. Acad. Sci. USA 79:5582; EPO Publ. Nos. 036 259 and 063 953; PCT Publ. No. WO 84/04541, for *Bacillus*; Miller et al. (1988) Proc. Natl. Acad. Sci. 85:856; Wang et al. (1990) J. Bacteriol. 172:949, for Campylobacter; Cohen et al. (1973) Proc. Natl. Acad. Sci. 69:2110; Dower et al. (1988) Nucleic Acids Res. 16:6127; Kushner (1978) "An improved method for transformation of *E. coli* with ColE1-derived plasmids," In *Genetic Engineering: Proceedings of the International Symposium on Genetic Engineering* (eds. H. W. Boyer and S. Nicosia); Mandel et al. (1970) J. Mol. Biol. 53:159; Taketo (1988) Biochim. Biophys. Acta 949:318, for *Escherichia*; Chassy et al. (1987) FEMS Microbiol. Lett. 44:173, for *Lactobacillus*; Fiedler et al. (1988) Anal. Biochem 170:38, for *Pseudomonas*; Augustin et al. (1990) FEMS Microbiol. Lett. 66:203, for *Staphylococcus*; Barany et al. (1980) J. Bacteriol. 144:698; Harlander (1987) "Transformation of *Streptococcus lactis* by electroporation, in: Streptococcal Genetics (ed. J. Ferretti and R. Curtiss III); Perry et al. (1981) Infec. Immun. 32:1295; Powell et al. (1988) Appl. Environ. Microbiol. 54:655; Somkuti et al. (1987) Proc. 4th Evr. Cong. Biotechnology 1:412, for *Streptococcus*.

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This tranScription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH)

(EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase, also provides useful promoter sequences, Myanohara et al. (1983) Proc. Natl. Acad. Sci. USA 80:1.

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. 4,876,197 and U.S. Pat. No. 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, Cohen et al. (1980) Proc. Natl. Acad. Sci. USA 77:1078; Henikoff et al. (1981) Nature 283:8.35; Hollenberg et al. (1981) Curr. Topics Microbiol. Immunol. 96:119; Hollenberg et al. (1979) "The Expression of Bacterial Antibiotic Resistance Genes in the Yeast *Saccharomyces cerevisiae*," in: *Plasmids of Medical. Environmental and Commercial Importance* (eds. K. N. Timmis and A. Puhler); Mercerau-Puigalon et al. (1980) Gene 11:163; Panthier et al. (1980) Curr. Genet. 2:109.

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Publ. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT Publ. No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588,684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. No. 4,546,083 and U.S. Pat. No. 4,870,008; EPO Publ. No. 324 274). Additional leaders employing an alpha-factor leader fragment that provides for secretion include hybrid alpha-factor leaders made with a presequence of a first yeast, but a pro-region from a second yeast alphafactor. (See e.g., PCT Publ. No. WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above-described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24, Botstein et al. (1979) Gene 8:17–24; pCl/1, Brake et al. (1984) Proc. Natl. Acad. Sci USA 81:4642–4646; and YRp17, Stinchcomb et al. (1982) J. Mol. Biol. 158:157. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. A high or low copy number vector may be selected, depending upon the effect of the vector and the foreign protein on the host.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome, Orr-Weaver et al. (1983) Methods in Enzymol. 101:228–245. An integrating vector may be directed to a specific locus in yeast by selecting the appropriate homologous sequence for inclusion in the vector. One or more expression construct may integrate, possibly affecting levels of recombinant protein produced, Rine et al. (1983) Proc. Natl. Acad. Sci. USA 80:6750. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions. Butt et al. (1987) Microbiol, Rev. 51:351.

Alternatively, some of the above-described components can be put together into transformation vectors. Transformation vectors are usually comprised of a selectable marker that is either maintained in a replicon or developed into an integrating vector.

Expression and transformation vectors, either extrachromosomal replicons or integrating vectors, have been developed for transformation into many yeasts. For example, expression vectors have been developed for, inter alia, the following yeasts: *Candida albicans*, Kurtz, et al. (1986) Mol. Cell. Biol. 6:142; *Candida maltosa*, Kunze, et al. (1985) J. Basic Microbiol. 25:141; *Hansenula polymorpha*, Gleeson, et al. (1986) J. Gen. Microbiol. 132:3459; Roggenkamp et al. (1986) Mol. Gen. Genet. 202:302; *Kluyveromyces fragilis*, Das, et al. (1984) J. Bacteriol. 158:1165; *Kluyveromyces lactis*, De Louvencourt et al. (1983) J. Bacteriol. 154:737; Van den Berg et al. (1990) Bio/Technology 8:135; *Pichia guillerimondii*, Kunze et al. (1985) J. Basic Microbiol. 25:141; *Pichia pastoris*, Cregg, et al. (1985) Mol. Cell. Biol. 5:3376; U.S. Pat. No. 4,837,148 and U.S. Pat. No. 4,929,555; *Saccharomyces cerevisiae*, Hinnen et al. (1978) Proc. Natl. Acad. Sci. USA 75:1929; Ito et al. (1983) J. Bacteriol. 153:163; *Schizosaccharomyces pombe*, Beach et al. (1981) Nature 300:706; and *Yarrowia lipolytica*, Davidow, et al. (1985) Curr. Genet. 10:380471 Gaillardin, et al. (1985) Curr. Genet. 10:49.

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., Kurtz et al. (1986) Mol. Cell. Biol. 6:142; Kunze et al. (1985) J. Basic Microbiol. 25:141, for *Candida*; Gleeson et al. (1986) J. Gen. Microbioy. 132:3459; Roggenkamp et al. (1986) Mol. Gen. Genet. 202:302, for *Hansenula*; Das et al. (1984) J. Bacteriol. 158:1165; De Louvencourt et al. (1983) J. Bacteriol. 154:1165; Van den Berg et al. (1990) Bio/Technology 8:135, for *Kluyveromyces*; Cregg et al. (1985) Mol. Cell. Biol. 5:3376; Kunze et al (1985) J. Basic Microbiol. 25:141; U.S. Pat. No. 4,837,148 and U.S. Pat. No. 4,929,555, for *Pichia*; Hinnen et al. (1978) Proc. Natl. Acad. Sci. USA 75;1929; Ito et al. (1983) J. Bacteriol. 153:163, for *Saccharomyces*; Beach et al. (1981) Nature 300:706, for *Schizosaccharomyces*; Davidow et al. (1985) Curr. Genet. 10:39; Gaillardin et al. (1985) Curr. Genet. 10:49, for *Yarrowia*.

E. Vaccines

Each of the *H. pylori* proteins discussed herein may be used as a sole vaccine candidate or in combination with one or more other antigens, the latter either from *H. pylori* or other pathogenic sources. Preferred are "cocktail" vaccines comprising, for example, the cytotoxin (CT) antigen, the CAI protein, and the urease. Additionally, the hsp can be added to one or more of these components. These vaccines may either be prophylactic (to prevent infection) or therapeutic (to treat disease after infection).

Such vaccines comprise *H. pylori* antigen or antigens, usually in combination with "pharmaceutically acceptable carriers", which include any carrier that does not itself induce the production of antibodies harmful to the individual receiving the composition." Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene®, 0.5% Tween 80®, and 0.5% Span 85® (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80®, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene®, 0.2% Tween 80®, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CFS), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-iso-glutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc., the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Oral formulations are most preferred for the *H. pylori* proteins. Dosage treatment may be a single dose schedule or a multiple dose schedule. The vaccine may be administered in conjunction with other immunoregulatory agents.

F. Immunodiagnostic Assays

*H. pylori* antigens can be used in immunoassays to detect antibody levels (or conversely *H. pylori* antibodies can be used to detect antigen levels) and correlation can be made with gastroduodenal disease and with duodenal ulcer in particular. Immunoassays based on well defined, recombinant antigens can be developed to replace the invasive diagnostics methods that are used today. Antibodies to *H. pylori* proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

G. Examples

The examples presented below are provided as a further guide to the practitioner of ordinary skill in the art and are not to be construed as limiting the invention in any way.

i. *H. pylori* cytotoxin (CT) antigen

1. Materials and Methods

For general materials and methods relating to *H. pylori* growth and DNA isolation, see sections ii and iii below, relating to CAI antigen and hsp, respectively.

a. Cloning

Two mixtures of degenerate oligonucleotides were synthesized using an Applied Biosystems model 380B DNA synthesizer. These mixtures were used at a concentration of 4 micromolar in a 100 microliter polymerase chain reaction with 200 nanograms of purified DNA using the Genamp PCR kit according to the manufacturers instructions. The reaction was incubated for 1 minute at 94 degrees centigrade, 2 minutes at 48 degrees centigrade and 2 minutes at 56 degrees centigrade. The reaction mix was subjected to 30 cycles of these conditions.

Analysis of the products of this reaction by agarose gel electrophoresis revealed a prominent approximately 87 bp DNA fragment. After digestion with the restriction enzymes XbaI and EcoRI, the fragment was ligated to the Bluscript SK+ (Stratgene) plasmid which had previously also been digested with XbaI and EcoRI. The ligation mixture was used to transform competent *E. coli* by electroporation at 2000 V and 25 microfarads using (200Ω) a BioRad Gene Pulser (California). Transformed *E. coli* were selected for growth on L-agar plates containing 100 micrograms per milliliter ampicillin. Plasmid DNA was extracted from positive *E. coli* isolates and subjected to sequence analysis using the Sequenase 2 (United States Biochemical Corporation) DNA sequencing kit according to the manufacturers instructions.

b. Preparation of Libraries (1) Library of HindIII Fragments

Seven micrograms of purified DNA were digested to completion with the restriction enzyme HindIII. Three micrograms of Bluescript SK+ plasmid DNA were digested to completion with HindIII then treated with calf intestinal phosphatase. Both DNA mixtures were purified by agitation with a water saturated phenol then precipitated by addition of ethyl alcohol to 67% V/V. Both DNAs were resuspended in 50 microliters of water. 0.7 micrograms of DNA fragments were mixed with 0.3 micrograms of Bluescript DNA in 50 microliters of a solution containing 25 mM Tris ph 7.5, 10 mM MgCl2 and 5 units of T4 DNA ligase. This mix was incubated at 15 deg. centigrade for 20 hours after which the DNA was extracted with water saturated phenol and precipitated from ethyl alcohol. The DNA was subsequently resuspended in 50 microL. of water. Introduction of 1 microL of this DNA into *E. coli* by eletroporation resulted in approximately 3000–10,000 ampicillin resistant bacterial colonies.

2) Library of EcoRI Fragments.

About 0.7 microg. of EcoRI digested DNA was purified and mixed with 0.45 micrograms of Bluescript SK+ plasmid which had been previously digested with EcoRI and treated with calf intestinal phosphatase. The fragments were ligated in 50 microL of solution. After purification and precipitation, the DNA was resuspended in 50 microL of water. Electroporation of *E. coli* with 1 microL of this solution resulted in approximately 200 ampicillin resistant bacterial colonies.

In order to identify suitable restriction fragments from the genome for further cloning, the plasmid was uniformly labeled with 32p and used as a probe to analyze DNA from the strain CCUG digested with various restriction enzymes, separated on agarose gel electrophoresis and transferred to nitrocellulose filter. The probe revealed a unique approximately 3.5 kb HindIII restriction fragment. A library of HindIII digested DNA fragments was prepared and cloned in the Bluescript plasmid vector. This library was screened with 32p labeled DNA corresponding to the 87 bp fragment previously cloned. Two clones containing identical approximately 3.3 kbp hindIII fragments were identified. DNA sequencing of these HindIII fragments revealed sequences capable of coding for the 23 amino acids corresponding to the amino terminus of the previously described 87 kDa cytotoxin. These sequences comprised part of an open reading frame of approximately 300 nucleotides which terminated at the extremity of the fragment delimited by a HindIII restriction site. The sequence also revealed the existence of an EcoRI restriction site within the putative open reading frame 120 bp away from the HindIII site.

A 32p labeled probe corresponding to the sequences between the EcoRI site and the HindIII site was used to screen a library of EcoR fragments from DNA cloned in the Bluescript SK vector. This probe revealed two clones containing approximately 7.3 kbp fragments. DNA sequencing of these fragments revealed a continuous open reading frame which overlapped with the sequences determined from the 3.2 kbp HindIII fragments. The DNA sequence of these overlapping fragments and the conceptual translation of the single long open reading frame contained are shown in FIGS. 1 and 2, respectively.

It should be noted that these clones were found to be extremely unstable. The initial colonies identified in the screening were so small as to be difficult to detect. Expansion of these clones by traditional methods of subculturing for 16–18 hours resulted in very heterogeneous populations of plasmids due to DNA rearrangement and deletion. Sufficient quantities of these clones were grown by subculturing for 8–10 hours in the absence of antibiotic selection. In this fashion, although yields of plasmid were relatively low, selection and outgrowth of bacteria containing viable rearranged plasmid were avoided.

C. Screening of DNA Libraries

The product of the PCR reaction which contained the predominant 87 bp fragment was labeled with 32p by the random priming method using the Prime-a-gene kit (Promega). This labeled probe was used in a hybridization reaction with DNA from approximately 3000 bacterial clones immobilized on nitrocellulose filters. The hybridization reaction was carried out at 60 degrees centigrade in a solution of 0.3M NaCl. A positive bacterial clone was expanded and plasmid DNA was prepared. The plasmid contained an insert of approximately 3.3 kb of DNA and was designated TOXHH1.

A 120 bp fragment containing the sequences between position 292 and 410 shown in FIG. 1 was derived from the plasmid TOXHH1 and used to screen approximately 400 colonies of the library of EcoRI fragments. A positive clone was isolated which contained approximately 7.3 kb of DNA sequences and was designated TOXEE1.

The nucleotide sequence shown in FIG. 1 was derived from the clones TOXHH1 and TOXEE1 using the Sequenase 2 sequencing kit. The nucleotides between position 1 and 410 in FIG. 1 were derived from TOXHH1 and those between 291 and 3507 were derived from TOXEE1. *E. coli* containing plasmids TOXHH1 and TOXEE1 have been deposited with the American Type Culture Collection, see below.

D. Preparation of Antisera Against the Cytotoxin

A DNA fragment corresponding to nucleotides 116–413 of the sequence shown in FIG. 1 was cloned into the bacterial expression vector pex 34 A, such that on induction of the bacterial promoter, a fusion protein was produced which contained a part of the MS2 polymerase polypeptide fused to the amino acids of the cytotoxin polypeptide and including the 23 amino acids previously identified. Approximately 200 micrograms of this fusion protein were partially purified by acrylamide gel electrophoresis and used to immunize rabbits by standard procedures.

Antisera from these rabbits taken after 3 immunizations spaced 1 month apart was used to probe protein extracts from a cytotoxin positive and a cytotoxin negative strain of *H. pylori* in standard immunoblotting experiments. The antisera revealed a polypeptide which migrated on denaturing polyacrylamide gel electrophoresis with an apparent molecular mass of 100 kDa. This polypeptide was detected in protein extracts of the cytotoxin positive but not the cytotoxin negative strain. Serum collected prior to immunization did not react with this polypeptide.

E. Partial Purification of Vacuolating Activity

Total *H. pylori* membranes at a concentration of 6 mg/ml were solubilized in a solution of 1% CHAPS, 0.5 M NaCl, 10 mM Hepes pH 7.4, 2.5 mM EDTA, 20% sucrose for 1 hour at 4° C. This mixture was then applied to a discontinuous sucrose gradient containing steps of 30%, 35%, 40% and 55% sucrose and subjected to ultracentrifugation for 17 hours at 20000×g. The gradient was fractionated and each fraction was tested for vacuolating activity and for urease activity. Vacuolating activity associated with urease activity was found in several fractions of the gradient. A peak of vacuolating activity was also found in the topmost fractions of the gradient and these fractions were essentially free of urease activity.

This urease-independent vacuolating activity was further fractionated by stepwise precipitation with ammonium sulphate between concentrations of 20% to 34%. Denaturing polyacrylamide gel electrophoresis of the proteins precipitated at different concentrations of ammonium sulphate revealed a predominant polypeptide of about 100 kDa which copurified with the vacuolating activity. This polypeptide was recognised by the rabbit antisera raised against the recombinant fusion protein described above.

2. Results

Two overlapping fragments corresponding to about 10 kbp of the *H. pylori* genome have been cloned. These clones contain a gene consisting of 3960 bp (shown in FIG. 1) which is capable of coding for a polypeptide of 1296 amino acids (shown in FIG. 2). The molecular weight of this putative polypeptide is 139.8 kd. The nucleotide sequence AGGAAG 9 bp upstream of the methionine codon at position 18 in FIG. 1 resembles closely the consensus Shine-Dalgarno sequence and supports the hypothesis that this methionine represents the initiator methionine for synthesis of the polypeptide. A 30 bp nucleotide sequence which begins 10 bp downstream of the putative stop codon at position 3906 in FIG. 1 resembles closely the the structure of prokaryotic transcription terminators and is likely to represent the end of the messenger RNA coding sequences.

The cytotoxin gene is defined as coding for a polypeptide precursor of the *H. pylori* vacuolating activity by the following criteria:

(i) The putative polypeptide contains the 23 amino acid sequence (FIG. 2, positions 34–56) identified as the amino terminus of the previously described 87 kDa vaculating protein, Clover et al., J. Biol. Chem. 267:10570–75 (1992). This sequence is preceded by 33 amino acids which resemble prokaryotic leader sequences; thus, this sequence is likely to represent the amino terminus of a mature protein;

(ii) Rabbit antisera specific for a 100 amino acid fragment of the putative polypeptide containing the proposed amino terminus recognized a 100 kDa polypeptide in a cytotoxin positive but not a cytotoxin negative strain of H. pylori. This 100 kDa polypeptide copurifies with vacuolating activity from H. pylori membranes.

In sum, the gene described herein codes for an approximately 140 kDa polypeptide which is processed to a 100 kDa polypeptide involved in H. pylori cytotoxic activity. The 87 kDa polypeptide previously described must result from either further processing of the 100 kDa polypetide or from proteolytic degradation during purification.

ii. H. pylori CAI antigen

1. Materials and Methods a. Origin of Materials

Clones A1, 64/4, G5, A17, 24 and 57/D were obtained from the lambda gt11 library. Clone B1 was obtained from a genomic plasmid library of HindIII fragments. 007 was obtained by PCR. The H. pylori strains producing the cytotoxin were: G10, G27, G29, G32, G33, G39, G56, G65, G105, G113A. The noncytotoxic strains were: G12, G21, G25, G47, G50, G204. They were isolated from endoscopy biopsy specimens/at the Grosseto Hospital, (Tuscany, Italy). The strain CCUG 17874 (cytotoxin positive), was obtained from the Culture Collection of the University of Gotheborg. The noncytotoxic strains Pylo 2U+ (urease positive) and Pylo 2U− (urease negative) were obtained from F. Megraud, Centre Hospitalier, Bordeaux (France). E. coli strains DH10B (Bethesda Research Laboratories), TG1, K12 delta H1 delta trp, Y1088, Y1089, Y1090 are known in the art. Plasmid Bluescript SK+ (Stratagene, La Jolla, Calif.) was used as a cloning vector. The pEx34 a, b, c plasmids for the expression of MS2 fusion proteins have been previously described. The lambda gt11 phage vector used for the expression library is from the lambda gt11 cloning system kit (Bethesda Research Laboratories). E. coli strains were cultured in LB medium (24). H. pylori strains were plated onto selective media (5% horse blood, Columbia agar base with Dent or Skirrow's antibiotic supplement, 0.2% cyclodextrin) or in Brucella broth liquid medium containing 5% fetal bovine serum (6) or 0.2% cyclodextrin (25).

b. Growth of H. pylori and DNA Isolation

H. pylori strains were cultured in solid or liquid media for 3 days at 37° C., both in microaerophilic atmosphere using Oxoid (Basingstoke, England) or Becton and Dickinson (Cockeysville, Md.) gas pack generators or in an incubator containing air supplemented with 5% CO2, (26). The bacteria were harvested and resuspended in STE (NaCl 0.1M, Tris-HCl 10 mM pH 8, EDTA 1 mM pH 8) containing lysozyme at a final concentration of 100 micrograms/ml and incubated at room temperature for 5 min. To lyse the bacteria SDS was added to a final concentration 1% and heated at 65° C. After the addition of proteinase K at final concentration of 25 micrograms/ml the solution was incubated at 50° for 2 hours. The DNA was purified by CsCl gradient in the presence of ethidium bromide, precipitated with 77% ethanol and recovered with a sealed glass capillary.

c. Construction and Screening of a Lambda gt11 Expression Library

To generate the lambda gt11 expression library, genomic DNA from the CCUG 17874 strain partially digested with the restriction enzymes HaeIII and AluI was used. After fractionation on 0.8% agarose gel, the DNA between 0.6 and 8 Kb in size was eluted using a Costar Spin-X (0.22 micron) microcentrifuge filter. The products from each digestion were combined, and used to construct the expression library, using the lambda gt11 cloning system kit (Bethesda Research Laboratories) and the Gigapack II Gold packaging kit (Stratagene, La Jolla, Calif.). The library that contained $0.8-1\times10^6$ recombinant phages was amplified in E. coli Y1088, obtaining 150 ml of a lysate with a titer of $10^9$ phages/ml, 85% of which were recombinant and had an average insert size of 900 base pairs. Immunological screening was performed by standard procedures, using the Protoblot system (Promega, Madison, Wis.).

d. Construction of Plasmid Libraries

Attempts to make complete genomic libraries of partially digested chromosomal DNA, using standard vectors such as EMBL4 or lambda Dash encountered the difficulties described also by many authors in cloning H. pylori DNA and failed to give satisfactory libraries. Therefore, partial libraries were obtained using genomic DNA from strains CCUG 17874, G39 and G50 digested with the restriction enzyme HindIII, cloned in the Bluescript SK+. DNA ligation, electroporation of E. coli DH 10B, screening, and library amplification have been performed. Libraries ranging from 70000 to 85000 colonies with a background not exceeding the 10% were obtained.

E. DNA Manipulation and Nucleotide Sequencing

DNA manipulation was performed using standard procedures. DNA sequencing was performed using Sequenase 2.0 (USB) and the DNA fragments shown in FIG. 3 subcloned in Bluscript KS+. Each strand was sequenced at least three times. The region between nucleotides 1533 and 2289, for which a DNA clone was not available, was amplified by PCR and sequenced using asymmetric PCR, and direct sequencing of amplified products. The overlapping of this region, was confirmed by one and double side anchored PCR: an external universal anchor (5'-GCAAGCTTATC-GATGTCGACTCGAGCT-3'(SEQ ID NO:1)/5'-GACTC-GAGTCGACATCGA-3'(SEQ ID NO:8) containing a protruding 5' HindIII sequence, and the recognition sites of ClaI, SalI, XhoI, was ligated to primer-extended DNA and amplified. A second round of PCR using nested primers was then used to obtain fragments of DNA suitable for cloning and sequencing. DNA sequence data were assembled and analyzed with the GCG package (Genetics Computer Group, Inc., Madison, Wis.) running on a VAX 3900 under VMS. The GenBank and EMBL databases were examined using the EMBL VAXcluster.

f. Protein Preparation and ELISA

Protein extracts were obtained by treating H. pylori pellets with 6 M guanidine. Western blotting, SDS-PAGE, electroelution were performed by standard procedures. Fusion proteins were induced and purified by electrocution or by ion exchange chromatography. Purified proteins were used to immunize rabbits and to coat microtiter plates for ELISA assays. Sera from people with normal mucosa, blood donor and patients were obtained from A. Ponzetto (Torino, Italy) Clinical diagnosis was based on histology of gastric biopsies. Vacuolating activity of samples was tested on HeLa cells as described by Cover et al. Infect. Immun. 59:1264–70 (1991).

2. Results a. Immunodominance and Cytotoxicity

Western blots of H. pylori guanidine extracts probed with sera from patients width gastroduodenal disease showed that a protein of 130 kDa that is a minor component in the Coomassie blue stained gel was strongly recognized by all sera tested. The CAI protein was electroeluted and used to raise a mouse serum that in a Western blot recognized only this protein. This serum was then used to detect by Western blotting the CAI protein in extracts of the *H. pylori* strains. The antigen was present in the all 10 strains that had vacuolizing activity on HeLa cells while it was absent in the eight strains that did not have such activity; in addition, the size of the protein varied slightly among the strains. The CAI antigen was not detected by western blotting in the other species tested such as *Campylobacter ieiuni, Helicobacter mustelae, E. coli*, and *Bordetella pertussis*.

b. Structure of the cai Gene $10^6$ clones of the lambda gt11 expression library were screened using the mouse serum-specific for the CAI antigen and with a pool of sera from patients with gastroduodenal diseases. The mouse serum detected positive clones at a frequency of $3\times10^{-3}$ Sequence analysis of 8 clones revealed that they were all partially overlapping with clone A1 shown in FIG. 3. The pool of human sera identified many clones containing different regions of the cai gene, including clones 57/D, 64/4 and 24 and several clones overlapping clone A1.

In FIG. 3, clones A1, 64/4, G5, A17, 24, and 57/D were obtained from the lambda gt11 library. Clone B1 was obtained from a plasmid library of HindIII fragments. *E. coli* containing plasmids 57/D, 64/4, B1 (B/1), and P1–24 (the latter most plasmid from nucleotide 2150 to 2650) have been deposited with the American Type Culture Collection (ATCC), see below. 007 was obtained by PCR. The open-reading frame is shown at the bottom of FIG. 3. Arrows indicate the position and direction of the synthetic oligo-nucleotides used as primers for sequencing, and the position of insertion of the repeated sequence of G39 is shown. The nucleotide and amino acid sequence of one of the repeated sequences found in strain G39 is also shown. The capital letters indicate the sequences D1, D2, and D3 duplicated from the cai gene, the small letters indicate the nucleotide and amino acid linkers, P=promoter, and T=terminator.

The nucleotide sequence of the entire region was determined using the clones derived from the lambda gt11 library, the clone B1 isolated from the HindIII plasmid library, and the fragment 007 that was obtained by PCR of the chromosomal DNA. Computer analysis of the 5925 nucleotide sequence revealed a long open reading frame spanning nucleotides 535 to 3977 that was in frame with the fusion proteins deriving from the lambda gt11 clones 6.4/4, 24 and A1 and A17. Clone 57/D contained an open reading frame only in the 3' end of cloned fragment and therefore could not make a gene fusion with the beta galactosidase gene of lambda gt11. The presence of an immunoreactive protein in the lambda gt11 clone 57/D could only be explained by the presence of an endogenous promoter driving the expression of a non fused protein. This hypothesis was proven to be true by subcloning in both direction the insert 57/4 into the Bluescript plasmid vector and showing that an immunoreactive protein was obtained in both cases. A conclusive evidence that the gene identified was indeed coding for the CAI antigen was obtained by subcloning the inserts A17 and 64/4 in the pEx 34B plasmid vectors to obtain fusion proteins that were purified and used to immunize rabbits. The sera obtained, recognized specifically the CAI antigen band in cytotoxic H. Pylori strains.

The cai gene coded for a putative protein of 1147 amino acids, with predicted molecular weight of 128012.73 Daltons and an isoelectric point of 9.72. The basic properties of the purified protein were confirmed by two dimensional gel electrophoresis. The codon usage and the GC content (37%) of the gene were similar to that described for other *H. pylori* genes (13,26). A putative ribosome binding site: AGGAG, was identified 5 base pairs upstream from the proposed ATG starting codon. Computer search for promoter sequences of the region upstream from the ATG start codon, identified sequences resembling either −10 or −35 regions, however, a region with good consensus to an *E. coli* promoter, or resembling published *H. pylori* promoter sequences was not found. Primer extension analysis of purified *H. pylori* RNA showed that 104 and 214 base pairs upstream from the ATG start codon there are two transcriptional start sites. Canonical promoters could not be identified upstream from either transcriptional initiation sites. The expression of a portion of the CAI antigen by clone 57/D suggests that *E. coli* is also recognizing a promoter in this region, however, it is not clear whether *E. coli* recognizes the same promoters of *H. pylori* or whether the *H. pylori* DNA that is rich in A-T provides *E. coli* with regions that may act as promoters. A rho independent terminator was identified downstream from the stop codon. In FIG. 4, the AGGAG ribosome binding site and terminator are underlined, and the repeated sequence and motif containing 6 asparagines (SEQ ID NO:23) are boxed. The CAI antigen was very hydrophilic, and did not show obvious leader peptide or transmembrane sequences. The most hydrophilic region was from amino acids 600 to 900, where also a number of unusual features can be observed: the repetition of the sequences EFKNGKNKDFSK (SEQ ID NO:9) and EPIYA (SEQ ID NO:10), and the presence of a stretch of six contiguous asparagines (boxed in FIG. 4)(SEQ ID NO:23) which is encoded by the sequence of SEQ ID NO:24.

Diversity of the gene appears to be generated by internal duplications. To find out the mechanism of size heterogeneity of the CAI proteins in different strains, the structure of one of the strains with a larger CAI protein (G39) was analyzed using Southern blotting, PCR and DNA sequencing. The results showed that the cai gene of G39 and CCUG 17874 were identical in size until position 3406, where the G39 strain was found to contain an insertion of 204 base pairs, made by two identical repeats of 102 base pairs. Each repeat was found to contain sequences deriving from the duplication of 3 segments of DNA (sequences D1 (SEQ ID NO:13), D2 (SEQ ID NO:15) and D3 (SEQ ID NO:18) in FIG. 3) coming from the same region of the cai gene and connected by small linker sequences. A schematic representation of the region where the insertion occurred and of the insertion itself is shown in FIG. 3. The nucleotide sequence of the insertion shown (SEQ ID NO:11) has the deduced amino acid sequence shown (SEQ ID NO:12).

To investigate why the CAI antigen was absent in the noncytotoxic strains, DNA from two of them (G50 and G21), was digested with EcoRI, HindIII and HaeIII restriction enzymes, and tested by Southern blotting using two probes internal to the cai gene, spanning nucleotides 520–1840 and 2850–4331 respectively. Both probes recognized strongly hybridizing bands in strains CCUG 17874 and G39. The bands varied in size in the two strains, in agreement with the gene diversity. However, neither probe hybridized the G50 and G21 DNA. This showed that the noncytotoxic strains tested do not contain the cai gene.

e. Serum Antibodies

The presence of serum antibodies against the CAI antigen correlated with gastroduodenal diseases. To study the quantitative antibody response to the CAI antigen, the fusion protein produced by the A17 fragment subcloned in pEx34 was purified to homogeneity and used to coat microtiter plates for an ELISA test. In this assay, the patients with gastroduodenal pathologies had an average ELISA titer that was significantly higher than that found in randomly selected blood donors and people with normal gastric mucosa. To evaluate whether the antibody titer correlated with a particular gastroduodenal disease, the sera from patients with known histological diagnosis were tested in the ELISA assay. Patients with duodenal ulcer had an average antibody titer significantly higher than all the other diseases. Altogether, the ELISA was found to be able to predict 75.3% of the patients with any gastroduodenal disease and 100% of the patients with duodenal ulcer.

In one particular ELISA, a recombinant protein containing 230 amino acids deriving from CAI antigen was identified by screening an expression library of *H. pylori* DNA using an antiserum specific for the protein. The recombinant antigen was expressed as a fusion protein in *E. coli*, purified to homogeneity, and used to coat microtiter plates. The plates were then incubated for 90 minutes with a 1/2000 dilution of goat anti-human IgG alkaline phosphatase conjugate. Following washing, the enzyme substrate was added to the plates and the optical density at 405 nm was read 30 minutes later. The cutoff level was determined by the mean absorbance plus two standard deviations, using sera from 20 individuals that had neither gastric disease nor detectable anti-*H. pylori* antibodies in Western blotting. The ELISA assay was tested on the peripheral blood samples of eighty-two dyspeptic patients (mean age 50.6±13.4 years, ranging from 28 to 80) undergoing routine upper gastrointestinal endoscopy examination. The gastric antral mucosa of patients was obtained for histology and Giemsa strain. Twenty of the patients had duodenal ulcer, 5 had gastric ulcer, 43 had chronic active gastritis type B, 8 had duodenitis and 6 had a normal histology of gastric mucosa. All of the patients with duodenal ulcer had an optical density value above the cutoff level. The patients with duodenitis, gastric ulcer, and chronic gastritis, had a positive ELISA value in 75%, 80% and 53.9% of the cases, respectively. The agreement between ELISA and histological Giemsa staining was 95% in duodenal ulcer, 98% in duodenitis, 80% in gastric ulcer and 55.8% in chronic gastritis. This assay gives an excellent correlation with duodenal ulcer disease (p 0.0005).

iii. Heat Shock Protein (hsp)

1. Materials and Methods a. *H. pylori* Strains and Growth Conditions

*H. pylori* strains used were: CCUG 17874, G39 and G33 (isolated from gastric biopsies in the hospital of Grosseto, Italy), Pylo 2U+ and Pylo 2U− (provided by F. Megraud, hospital Pellegzin, Bordeaux, France), BA96 (isolated by gastric biopsies at the University of Siena, Italy). Strain Pylo 2U+ is noncytotoxic; strain Pylo 2U− is noncytotoxic and urease-negative. All strains were routinely grown on Columbia agar containing 0.2% of cyclodextrin, 5 µg/ml of cefsulodin and 5 µg/ml of amphotericin B under microaerophilic conditions for 5–6 days at 37° C. Cells were harvested and washed with PBS. The pellets were resuspended in Laemmli sample buffer and lysed by boiling.

Sera of patients affected by gastritis and ulcers (provided by A. Ponzetto, hospital "Le Molinette", Torino, Italy) and sera of patients with gastric carcinoma (provided by F. Roviello, University of Siena, Italy) were used.

b. Immunoscreening of the library Five hundred thousand plaques of a λgt11 *H. pylori* DNA expression library were mixed with 5 ml of a suspension of *E. coli* strain Y1090 grown O/N in LB with 0.2% Maltose and 10 mM $MgSO_4$, and resuspended in 10 mM $MgSO_4$ at 0.5 O.D. After 10 minutes incubation at 37° C., 75 ml of melted TopAgarose were poured in the bacterial/phage mix and the whole was plated on BBL plates (50,000 plaques/plate). After 3.5 hrs incubation of the plated library at 42° C., nitrocellulose filters (Schleicher and Schuell, Dassel, Germany), previously wet with 10 mM IPTG, were set on plates and incubation was prolonged for 3.5 hrs at 37° C. and then O/N at 4° C. Lifted filters with lambda proteins were rinse in PBS, and saturated in 5% nonfat dried milk dissolved in TBST (10 mM TRIS pH 8, 100 mM NaCl, 5M $MgCl_2$) for 20'. The first hybridization step was performed with the sera of patients; to develop and visualize positive plaques we used an anti human Ig antibody alkaline phosphatase conjugated (Cappel, West Chester, Pa.) and the NBT/BCIP kit (Promega, Madison, Wis.) in AP buffer (100 mM Tris pH 9.5, 100 mM NaCl, 5 mM $MgCl_2$) according to the manufacturer instructions.

c. Recombinant DNA Procedures

Reagents and restriction enzymes used were from Sigma (St. Louis, Mo.) and Boehringer (Mannheim, Germany). Standard techniques were used for molecular cloning, single-stranded DNA purification, transformation in *E. coli*, radioactive labeling of probes, colony screening of the *H. pylori* DNA genomic library, Southern blot analysis, PAGE and Western blot analysis.

d. DNA Sequence Analysis

The DNA fragments were subcloned in Bluescript SK+ (Stratagene, San Diego, Calif.). Single-stranded DNA sequencing was performed by using [$^{33}$P]adATP (New England Nuclear, Boston, Mass.) and the Sequenase kit (U.S. Biochemical Corp., Cleveland, Ohio) according to the manufacturer instructions. The sequence was determined in both strands and each strand was sequenced, on average, twice. Computer sequence analysis was performed using the GCG package.

e. Recombinant Proteins

MS2 polymerase fusion proteins were produced using the vector pEX34A, a derivative of pEX31. Insert Hp67 (from nucleotide 445 to nucleotide 1402 in FIG. 5), and the EcoRI linkers were cloned in frame into the EcoRi site of the vector. In order to confirm the location of the stop codon, the HpG3' HindIII fragment was cloned in frame into the HindIII site of pEX34A. Recombinant plasmids were transformed in *E. coli* K12:H1 Δtrp. In both cases after induction, a fusion protein of the expected molecular weight was produced. In the case of the EcoRI/EcoRI fragment, the fusion protein obtain after induction was electroeluted to immunize rabbits using standard protocols.

2. Results a. Screening of an Expression Library and Cloning of *H. pylori* hsp

In order to find a serum suitable for the screening of an *H. pylori* DNA expression library, sonicated extracts of *H. pylori* strain CCUG 17874 were tested in Western blot analysis against sera of patients affected by different forms of gastritis. The pattern of antigen recognition by different sera was variable, probably due to differences in the individual immune response as well as to the differences in the antigens expressed by the strains involved in the infection.

Serum N°19 was selected to screen a Δgt11 *H. pylori* DNA expression library to identify *H. pylori* specific antigens, expressed in vivo during bacterial growth. Following screening of the library with this serum, many positive clones were isolated and characterized. The nucleotide sequence of one of these, called Hp67, revealed an open-reading frame of 958 base-pairs, coding for a protein with high homology to the hsp60 family of heat-shock proteins, Ellis, Nature 358:191–92 (1992). In order to obtain the entire coding region, we used fragment Hp67 as a probe on Southern blot analysis of *H. pylori* DNA digested with different restriction enzymes. Probe Hp67 recognized two HindIII bands of approximately 800 and 1000 base-pairs, respectively. A genomic *H. pylori* library of HindIII-digested DNA was screened with probe Hp67 and two positive clones (HpG5' and HpG3') of the expected molecular weight were obtained. *E. coli* containing plasmids pHp60G2 (approximately nucleotides 1 to 829) and pHp60G5 (approximately nucleotides 824 to 1838) were deposited with the American Type Culture Collection (ATCC).

b. Sequence Analysis

The nucleotide sequence analysis revealed an open-reading frame of 1638 base-pairs, with a putative ribosome binding site 6 base-pairs upstream the starting ATG. FIG. 5 shows the nucleotide and amino acid sequences of *H. pylori* hsp. The putative ribosome-binding and the internal HindIII site are underlined. Cytosine in position 445 and guanine in position 1402 are the first and last nucleotide, respectively, in fragment Hp67. Thymine 1772 was identified as the last putative nucleotide transcribed using an algorithm for the localization of factor-independent terminator regions. The open-reading frame encoded for a protein of 546 amino acids, with a predicted molecular weight of 58.3 KDa and a predicted pI of 5.37. The codon preference of this gene is in agreement with the *H. pylori* codon usage.

The analysis of the hydrophylicity profiles revealed a protein mostly hydrophilic, without a predicted leader peptide or other transmembrane domains. The amino terminal sequence showed 100% homology to the sequence of 30 amino acids determined by Dunn et al., Infect. Immun. 60:1946–51 (1992) on the purified protein and differed by only on reside (Ser42 instead of Lys) from the sequence of 44 amino acids published by Evans et al, Infect. Immun. 60:2125–27 (1992). (Evans et al., 1992). The N-terminal sequence of the mature hsp protein did not contain the starting methionine, indicating that this had been removed after translation.

c. Homology with hsp60 Family

The amino acid sequence analysis showed a very strong homology with the family of heat-shock proteins hsp60, whose members are present in every living organism. Based on the degree of homology between hsp60 proteins of different species, *H. pylori* hsp belongs to the subgroup of hsp60 proteins of Gram negative bacteria; however, the degree of homology to the other proteins of the hsp60 family is very high (at least 54% identity).

d. Expression of Recombinant Proteins and Production of a Polyclonal Antiserum

The inserts of clone Hp67 and of clone HpG3' were subcloned in the expression vector pEX34A in order to express these open-reading frames fused to the aminoterminus of the MS2 polymerase. The clones produced recombinant proteins of the expected size and were recognized by the human serum used for the initial screening. The fused protein derived from clone Hp67 was electroeluted and used to immunize rabbits in order to obtain anti-hsp specific polyclonal antisera. The antiserum obtained recognized both fusion proteins, and a protein of 58 KDa on whole-cell extracts of several strains of *H. pylori* tested, including a urease-negative strain and noncytotoxic strains.

Hsp has been shown to be expressed by all the *H. Pylori* strains tested and its expression is not associated with the presence of the urease or with the cytotoxicity. The protein recognized by the anti-hsp antiserum was found in the water soluble extracts of *H. pylori* and copurified with the urease subunits. This suggests a weak association of this protein with the outer bacterial membrane. Thus, hsp can be described as urease-associated and surface exposed. The cellular surface localization is surprising as most of the hsp homologous proteins are localized in the cytoplasm or in mitochondria and plastids. The absence of a leader peptide in hsp suggests that this is either exported to the membrane by a peculiar export system, or that the protein is released from the cytoplasm and is passively adsorbed by the bacterial membrane after death of the bacterium.

Hsp60 proteins have been shown to act as molecular chaperons assisting the correct folding, assembly and translocation of either oligomeric or multimeric proteins. The cellular localization of *H. pylori* hsp and its weak association with urease suggest that hsp may play a role in assisting the folding and/or assembly of proteins exposed on the membrane surface and composed of multiple subunits such as the urease, whose final quaternary structure is $A_6B_6$. Austin et al., J. Bacteriol. 174:7470–73 (1992) showed that the *H. pylori* hsp ultrastructure is composed of seven subunits assembled in a disk-shaped particle that further stack side by side in groups of four. This structure resembles the shape and dimension of the urease macromolecule and this could explain the common properties of these two macromolecules that lead to their copurification. *H. pylori* hsp gene, however, is not part of the urease operon. In agreement with the gene structure of other bacterial hsp60 proteins, it should be part of a dicistronic operon.

e. Presence of Anti-hsp Antibodies in Patients with Gastroduodenal Diseases

The purified fusion protein was tested by Western blot using sera of patients infected by *H. pylori* and affected by atrophic and superficial gastritis, and patients with duodenal and gastric ulcers: most of the sera recognized the recombinant protein. However, the degree of recognition greatly varied between different individuals and the antibody levels did not show any obvious correlation with the type of disease. In addition, antibodies against *H. pylori* antigens and in particular against hsp protein were found in most of the 12 sera of patients affected by gastric carcinoma that were tested. Although *H. pylori* hsp recognition could not be put in relation with a particular clinical state of the disease given the high conservation between *H. pylori* hsp and its human homolog, it is possible that this protein may induce autoimmune antibodies cross-reacting with the human counterpart. This class of homologous proteins has been implicated in the induction of autoimmune disorders in different systems. The presence of high titers of anti-*H. pylori* hsp antibodies, potentially cross-reacting with the human homolog in dispeptic patients, suggests that this protein has a role in gastroduodenal disease. This autoreactivity could play a role in the tissue damage that occurs in *H. pylori*-induced gastritis, thus increasing the pathogenic mechanisms involved in the infection of this bacterium.

The high levels of antibodies against such a conserved protein is somewhat unusual; due to the high homology between members of the hsp60 family, including the human one, this protein should be very well tolerated by the host immune system. The strong immune response observed in many patients may be explained in two different ways: (1) the immune response is directed only against epitopes specific for *H. pylori* hsp; (2) the immune response is directed against epitopes which are in common between *H. pylori* hsp and human homolog.

H. Deposit of Biological Materials

The following materials were deposited on Dec. 15, 1992 and Jan. 22, 1993 by Bioscine Sclavo, S.p.A. with the American Type Culture Collection (ATCC), 10801 University Boulevard, Manassas, Va. 20110-2209, phone (703) 365-2700, under the terms of the Budapest Treaty on the International Recognition of the Deposit of Microorganisms for Purposes of Patent Procedure. For the cytotoxin protein (CT):

ATCC No.: 69157 *E. coli* TG1 containing the plasmid TOXHH1

ATCC No.: n/a *E. coli* TG1 containing the plasmid TOXEE1

For the CAI protein:

ATCC No. 69158 *E. coli* TG1 containing the plasmid 57/D

ATCC No. 69159 *E. coli* TG1 containing the plasmid 64/4

ATCC No. 69160 *E. coli* TG1 containing the plasmid P1–24

ATCC No. 69161 *E. coli* TG1 containing the plasmid B/1

For the heat shock protein (hsp):

ATCC No. 69155 *E. coli* TG1 containing the plasmid pHp60G2

ATCC No. 69156 *E. coli* TG1 containing the plasmid pHp605.

These deposits are provided as convenience to those of skill in the art, and are not an admission that a deposit is required under 35 U.S.C. §112. The nucleic acid sequences of these deposits, as well as the amino acid sequences of the polypeptides encoded thereby, are incorporated herein by reference and should be referred to in the event of any error in the sequences described herein as compared with the sequences of the deposits. A license may be required to make, use, or sell the deposited materials, and no such license is granted hereby.

What is claimed is:

1. A purified polypeptide comprising the amino acid sequence of SEQ ID NO:5.

2. The purified polypeptide of claim 1 wherein said polypeptide is recombinantly produced.

3. A purified polypeptide comprising the amino acid sequence of SEQ ID NO:25.

4. An immunogenic composition comprising an immunologically effective amount of a purified recombinant polypeptide comprising the amino acid sequence of SEQ ID NO:25.

5. An immunogenic composition comprising an immunologically effective amount of a purified first polypeptide, which first polypeptide comprises at least 11–15 contiguous amino acids of the amino acid sequence of SEQ ID NO:5, wherein said first polypeptide comprises at least one of the amino acid sequences selected from the group consisting of SEQ ID NO:9, SEQ ID NO:10, and six contiguous asparagine residues, and an immunologically effective amount of a purified second polypeptide, which second polypeptide comprises at least ten contiguous amino acids of *Helicobacter pylori* heat shock protein, wherein said heat shock protein comprises the amino acid sequence of SEQ ID NO:6.

6. The immunogenic composition of claim 5 wherein said second polypeptide comprises at least fifteen contiguous amino acids of the *Helicobacter pylori* heat shock protein, wherein said heat shock protein comprises the amino acid sequence of SEQ ID NO:6.

7. A method of preparing an immunogenic composition comprising bringing into association:

(1) an immunologically effective amount of a purified polypeptide, which polypeptide comprises the amino acid sequence of SEQ ID NO:25, and (2) a pharmaceutically acceptable carrier.

8. A method of preparing an immunogenic composition comprising:

bringing into association (1) an immunologically effective amount of a purified first polypeptide, which first polypeptide comprises at least 11–15 contiguous amino acids of the amino acid sequence of SEQ ID NO:5, wherein said first polypeptide comprises at least one of the amino acid sequences selected from the group consisting of SEQ ID NO:9, SEQ ID NO:10, and six contiguous asparagine residues, and (2) a pharmaceutically acceptable carrier, and adding an immunologically effective amount of a purified second polypeptide, which second polypeptide comprises at least ten contiguous amino acids of *Helicobacter pylori* heat shock protein, wherein said heat shock protein comprises the amino acid sequence of SEQ ID NO:6.

9. The purified polypeptide of claim 3, wherein said polypeptide is recombinantly produced.

10. An immunogenic composition comprising an immunologically effective amount of a purified first polypeptide, which first polypeptide comprises at least 11–15 contiguous amino acids of the amino acid sequence of SEQ ID NO:5, wherein said first polypeptide comprises at least one of the amino acid sequences selected from the group consisting of SEQ ID NO:9, SEQ ID NO:10, and six contiguous asparagine residues, and an immunologically effective amount of a purified second polypeptide, wherein said second polypeptide comprises at least ten contiguous amino acids of *Helicobacter pylori* cytotoxin (CT) protein, wherein said CT protein comprises the amino acid sequence of SEQ ID NO:3.

11. The method of claim 7 wherein said purified polypeptide is a recombinant polypeptide.

12. The immunogenic composition of claim 10 wherein said second polypeptide comprises at least fifteen contiguous amino acids of the *Helicobacter pylori* CT protein, wherein said CT protein comprises the amino acid sequence of SEQ ID NO:3.

13. An isolated and purified immunogenic polypeptide comprising *Helicobacter pylori* cytotoxin associated immunodominant (CAI) antigen comprising the amino acid sequence of SEQ ID NO:25.

14. The polypeptide of claim 13, wherein said polypeptide is a recombinant polypeptide.

15. An isolated and purified immunogenic polypeptide encoded by a polynucleotide sequence comprising nucleotides 7–690 of the nucleotide sequence of SEQ ID NO:26.

16. An isolated immunogenic polypeptide encoded by the polynucleotide sequence of SEQ ID NO:4.

17. The method of claim 8 wherein said first purified polypeptide is a recombinant polypeptide.

18. An immunogenic composition comprising an immunologically effective amount of a purified polypeptide comprising the amino acid sequence of SEQ ID NO:25.

19. An immunogenic composition comprising an immunologically effective amount of a purified first polypeptide, wherein said first polypeptide comprises the amino acid sequence of SEQ ID NO:25, and an immunologically effective amount of a second polypeptide, which second polypeptide comprises at least ten contiguous amino acids of *Helicobacter pylori* heat shock protein, wherein said heat shock protein comprises the amino acid sequence of SEQ ID NO:6.

20. The immunogenic composition of claim 19 wherein said heat shock protein comprises the amino acid sequence of SEQ ID NO:6.

21. The immunogenic composition of claim 19 wherein said heat shock protein is a recombinant polypeptide.

22. The immunogenic composition of claim 19 wherein said first polypeptide comprises the amino acid sequence of SEQ ID NO:5.

23. The immunogenic composition of claim 19 wherein said first polypeptide is a recombinant polypeptide.

24. An immunogenic composition comprising an immunologically effective amount of a purified first polypeptide, wherein said first polypeptide comprises the amino acid sequence of SEQ ID NO:25, and an immunologically effective amount of a purified second polypeptide, which second polypeptide comprises at least ten contiguous amino acids of *Helicobacter pylori* cytotoxin protein, wherein said cytotoxin protein comprises the amino acid sequence of SEQ ID NO:3.

25. The immunogenic composition of claim 24 wherein said cytotoxin protein comprises the amino acid sequence of SEQ ID NO:3.

26. The immunogenic composition of claim 24 wherein said first polypeptide comprises the amino acid sequence of SEQ ID NO:5.

27. The immunogenic composition of claim 24 wherein said cytotoxin protein is a recombinant polypeptide.

28. The immunogenic composition of claim 24 wherein said first polypeptide is a recombinant polypeptide.

29. The immunogenic composition of claim 4 wherein said recombinant polypeptide comprises the amino acid sequence of SEQ ID NO:5.

30. The method of claim 7 wherein said polypeptide comprises the amino acid sequence of SEQ ID NO:5.

31. A method of preparing an immunogenic composition comprising bringing into association (1) an immunologically effective amount of a purified first polypeptide, which first polypeptide comprises the amino acid sequence of SEQ ID NO:25 and (2) an immunologically effective amount of a purified second polypeptide, which second polypeptide comprises at least ten contiguous amino acids of *Helicobacter pylori* cytotoxin protein, wherein said cytotoxin protein comprises the amino acid sequence of SEQ ID NO:3.

32. The method of claim 31 wherein said cytotoxin protein comprises the amino acid sequence of SEQ ID NO:3.

33. The method of claim 31 wherein said first polypeptide comprises the amino acid sequence of SEQ ID NO:5.

34. The method of claim 31 wherein said cytotoxin protein is a recombinant polypeptide.

35. The method of claim 31 wherein said first polypeptide is a recombinant polypeptide.

36. A method of preparing an immunogenic composition comprising bringing into association (1) an immunologically effective amount of a purified first polypeptide, which first polypeptide comprises the amino acid sequence of SEQ ID NO:25 and (2) an immunologically effective amount of a purified second polypeptide, which second polypeptide comprises at least ten contiguous amino acids of *Helicobacter pylori* heat shock protein, wherein said heat shock protein comprises the amino acid sequence of SEQ ID NO:6.

37. The method of claim 36 wherein said heat shock protein comprises the amino acid sequence of SEQ ID NO:6.

38. The method of claim 36 wherein said heat shock protein is a recombinant polypeptide.

39. The method of claim 36 wherein said first polypeptide comprises the amino acid sequence of SEQ ID NO:5.

40. The method of claim 36 wherein said first polypeptide is a recombinant polypeptide.

41. The immunogenic composition of claim 5 wherein said first polypeptide is a recombinant polypeptide.

42. The immunogenic composition of claim 5 wherein said second polypeptide is a recombinant polypeptide.

43. An immunogenic composition comprising an immunologically effective amount of a purified first polypeptide, which first polypeptide comprises at least 11–15 contiguous amino acids of the amino acid sequence of SEQ ID NO:5, wherein said first polypeptide comprises at least one of the amino acid sequences selected from the group consisting of SEQ ID NO:9, SEQ ID NO:10, and six contiguous asparagine residues, and an immunologically effective amount of a purified second polypeptide, wherein said second polypeptide comprises the amino acid sequence of SEQ ID NO:6.

44. The immunogenic composition of claim 10 wherein said first polypeptide is a recombinant polypeptide.

45. The immunogenic composition of claim 10 wherein said second polypeptide is a recombinant polypeptide.

46. An immunogenic composition comprising an immunologically effective amount of a purified first polypeptide, which first polypeptide comprises at least 11–15 contiguous amino acids of the amino acid sequence of SEQ ID NO:5, wherein said first polypeptide comprises at least one of the amino acid sequences selected from the group consisting of SEQ ID NO:9, SEQ ID NO:10, and six contiguous asparagine residues, and an immunologically effective amount of a purified second polypeptide, wherein said second polypeptide comprises the amino acid sequence of SEQ ID NO:3.

47. A method of preparing an immunogenic composition comprising: bringing into association an immunologically effective amount of a purified first polypeptide, which first polypeptide comprises at least 11–15 contiguous amino acids of the amino acid sequence of SEQ ID NO:5, wherein said first polypeptide comprises at least one of the amino acid sequences selected from the group consisting of SEQ ID NO:9, SEQ ID NO:10, and six contiguous asparagine residues, and an immunologically effective amount of a purified second polypeptide, which second polypeptide comprises at least ten contiguous amino acids of *Helicobacter pylori* heat shock protein, wherein said heat shock protein comprises the amino acid sequence of SEQ ID NO:6.

48. The method of claim 47 wherein said first polypeptide is a recombinant polypeptide.

49. The method of claim 47 wherein said second polypeptide is a recombinant polypeptide.

50. The method of claim 47 wherein said second polypeptide comprises the amino acid sequence of SEQ ID NO:6.

51. A method of preparing an immunogenic composition comprising: bringing into association an immunologically effective amount of a purified first polypeptide, which first polypeptide comprises at least 11–15 contiguous amino acids of the amino acid sequence of SEQ ID NO:5, wherein said first polypeptide comprises at least one of the amino acid sequences selected from the group consisting of SEQ ID NO:9, SEQ ID NO:10, and six contiguous asparagine residues, and an immunologically effective amount of a purified second polypeptide, which second polypeptide comprises at least ten contiguous amino acids of *Helicobacter pylori* cytotoxin protein, wherein said cytotoxin protein comprises the amino acid sequence of SEQ ID NO:3.

52. The method of claim 51 wherein said first polypeptide is a recombinant polypeptide.

53. The method of claim 51 wherein said second polypeptide is a recombinant polypeptide.

54. The method of claim 51 wherein said second polypeptide comprises the amino acid sequence of SEQ ID NO:3.

55. The method of claim 8 wherein said second purified polypeptide is a recombinant polypeptide.

* * * * *